(12) United States Patent
Allen

(10) Patent No.: US 11,940,433 B1
(45) Date of Patent: Mar. 26, 2024

(54) INTELLIGENT BUILDING MONITORING

(71) Applicant: 9 FOUNDATIONS, INC., Chestnut Hill, MA (US)

(72) Inventor: Joseph G. Allen, Chestnut Hill, MA (US)

(73) Assignee: 9 FOUNDATIONS, INC., Chestnut Hill (MA)

( * ) Notice: Subject to any disclaimer, the term of this patent is extended or adjusted under 35 U.S.C. 154(b) by 0 days.

(21) Appl. No.: 18/338,871

(22) Filed: Jun. 21, 2023

Related U.S. Application Data

(63) Continuation of application No. 18/137,979, filed on Apr. 21, 2023.

(60) Provisional application No. 63/384,225, filed on Nov. 17, 2022, provisional application No. 63/333,690, filed on Apr. 22, 2022.

(51) Int. Cl.
*G01N 33/00* (2006.01)

(52) U.S. Cl.
CPC ..... *G01N 33/0075* (2013.01); *G01N 33/0062* (2013.01); *G01N 2033/0068* (2013.01)

(58) Field of Classification Search
CPC .... G05B 23/0221; G05B 15/02; G05B 17/02; G05B 2219/2614; G05B 2219/2642; G05B 19/042; G05B 19/0428; G05B 13/04; G06Q 50/06; G01N 33/0075; F24F 11/30; F24F 11/46; F24F 11/63; F24F 11/56; F24F 11/00; F24F 11/65; F24F 2110/10; F24F 2110/20; F24F 2110/50; F24F 7/06; Y02B 30/70; Y02B 20/40; Y02P 90/02; G01D 21/00

USPC ...... 73/865.9; 236/49.3, 44 R; 454/256, 239; 700/275, 276, 291, 28, 19, 29, 9, 83; 702/179, 183, 188, 189, 130, 1, 184, 113, 702/33, 28, 19, 9, 182, 127, 81; 703/6, 703/13, 22, 4
See application file for complete search history.

(56) References Cited

U.S. PATENT DOCUMENTS

| 2011/0231320 A1* | 9/2011 | Irving .............. G06Q 30/08 713/300 |
| 2013/0204439 A1* | 8/2013 | Scelzi .............. G05B 11/01 702/61 |

(Continued)

FOREIGN PATENT DOCUMENTS

DE    102014109949 B4 *   6/2018   ......... G05B 23/0227

*Primary Examiner* — Jeffrey P Aiello
(74) *Attorney, Agent, or Firm* — Mintz Levin Cohn Ferris Glovsky and Popeo, P.C.

(57) ABSTRACT

A method includes receiving data characterizing a time-dependent first sensor data detected by a first sensor, a time-dependent second sensor data detected by a second sensor, a time-dependent third sensor data detected by a third sensor, a first set of threshold values associated with the first sensor, a second set of threshold values associated with the second sensor, and a third set of threshold values associated with the third sensor and a time window. The first, second, and third sensors are located in a first space of a building. The method further includes calculating a first performance index, a second performance index, and a third performance index. The method also includes classifying the first performance index, the second performance index, and the third performance index into one of a plurality of performance indicators. The method further includes assigning a performance rating score for a space based on the classification.

20 Claims, 22 Drawing Sheets

(56) References Cited

U.S. PATENT DOCUMENTS

| | | | |
|---|---|---|---|
| 2014/0330538 A1* | 11/2014 | Conklin | G01M 99/00 |
| | | | 702/189 |
| 2016/0109865 A1* | 4/2016 | Bojorges Rodríguez | |
| | | | G01R 21/133 |
| | | | 700/275 |
| 2019/0273671 A1* | 9/2019 | Alcala Perez | H04L 43/08 |
| 2021/0072742 A1 | 3/2021 | Wu et al. | |
| 2022/0092500 A1* | 3/2022 | Drees | G05B 13/021 |
| 2023/0109096 A1* | 4/2023 | Cella | G05D 1/0027 |
| | | | 702/184 |
| 2023/0244221 A1* | 8/2023 | Kim | G05B 19/4183 |
| | | | 700/97 |

\* cited by examiner

*FIG. 7*

INTELLIGENT BUILDING MONITORING

CROSS-REFERENCE TO RELATED APPLICATIONS

This application claims the benefit of U.S. application Ser. No. 18/137,979, filed on Apr. 21, 2023, which claims the benefit of U.S. Provisional Application No. 63/384,225, filed on Nov. 17, 2022, entitled "INTELLIGENT BUILDING MONITORING," which is hereby incorporated by reference in its entirety. This application also claims the benefit of U.S. Provisional Application No. 63/333,690, filed on Apr. 22, 2022, entitled "INTELLIGENT BUILDING MONITORING," which is hereby also incorporated by reference in its entirety.

TECHNICAL FIELD

The present disclosure is directed to building environment sensor systems.

BACKGROUND

Indoor air factors of a building (e.g., carbon-dioxide or $CO_2$ concentration, fine particulate matter or $PM_{2.5}$ concentration, etc.) can impact the health and wellbeing of the occupants of the building. Monitoring the building can help in identifying problems associated with the building, and determining the corresponding solutions. This can be done by installing various sensors (e.g., $CO_2$ sensors, $PM_{2.5}$ sensors, etc.) that can make real-time spot measurements of building conditions. The real-time spot measurements can assist with assessing the air conditions of the building, provided that the raw data are combined with additional information to aid in the interpretation of those data. Some conventional systems that utilize multiple sensors to determine real-time indoor air quality are challenged by the large amount of sensor data and thus often use techniques based on one-time spot measurements, which are unable to determine and identify long-term trends in building air quality.

SUMMARY

Various aspects of the disclosed subject matter may provide one or more of the following capabilities.

A method includes receiving data characterizing a time-dependent first sensor data detected by a first sensor, a time-dependent second sensor data detected by a second sensor, a first threshold value associated with the first sensor, a second threshold value associated with the second sensor and a time window. The first sensor and the second sensor are located in a first space of a building. The method further includes calculating a first performance index based on the first sensor data and the time window and a second performance index based on the second sensor data and the time window. The method also includes classifying the first performance index and the second performance index into one of a plurality of performance indicators wherein the classification of the first performance index and the second performance index is based on comparison of the first performance index and the second performance index with the first threshold value and the second threshold value, respectively. The method further includes determining a performance rating score for the first space by scoring the classification of first performance index and the second performance index within the plurality of performance indicators.

One or more of the following features can be included in any feasible combination.

In some implementations, calculating the first performance index includes selecting a first portion of the time-dependent first sensor data that temporally spans from a first time to a second time. The difference between the second time and the first time corresponds to the time window. The method also includes calculating the first performance index by averaging the first portion of the time-dependent first sensor data.

In some implementations, the method further includes calculating a third performance index. The calculating includes selecting a second portion of the time-dependent first sensor data that temporally spans from a third time to a fourth time. The difference between the fourth time and the third time corresponds to the time window. The method also includes calculating the third performance index by averaging the second portion of the time-dependent first sensor data. In some implementations, the method further includes classifying the first performance index to a first category of the plurality of categories, and classifying the third performance index to a second category of the plurality of categories. The method may include classifying the first performance index to a first category when the first performance index is greater than the first threshold value associated with the first sensor. The method may include classifying the second performance index to a second category when the second performance index is smaller than the first threshold value.

In some implementations, the method further includes rendering, in a graphical user interface, a first visual representation of the first performance indicator and a second visual representation of the second performance indicator; generating a first graphical object indicative of the first performance index; generating a second graphical object indicative of the third performance index; and rendering, in the graphical user interface, the first graphical object over the first visual representation and the second graphical object over the second visual representation. In some implementations, the first graphical object is rendered in a first region of the graphical user interface at a first time, wherein the first graphical object traverses from the first region of the graphical region to the first visual representation during a time period subsequent to the first time. In some implementations, the method further includes rendering, in a graphical user interface, a visual representation of at least one of the first performance indicator, the second performance indicator, and the performance rating score of the first space for a first time period; and rendering in a graphical user interface a second visual representation of at least one of the first performance indicator, the second performance indicator, and the performance rating score of the first space for a second time period.

In some implementations, the method further includes receiving environmental data including at least one of ventilation, infiltration and recirculation rates, heating filter type, airflow, space dimensions, and floor plans. The method may also include the step of determining a first sensor position for a first sensor and a second sensor position for a second sensor within the first space of the building.

In some implementations, the method further includes receiving data characterizing a time-dependent third sensor data detected by a third sensor, and a set of third threshold values associated with the third sensor, wherein the third sensor is located in the first space of the building, calculating a third performance index based on the third sensor data and the time window, classifying the third performance index into one of a plurality of performance indicators where the classification of the third performance index is based on a comparison of the third performance index with the third set of threshold values, and wherein determining the performance rating score for the first space further comprises scoring the classification of the third performance index within the plurality of performance indicators.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

These and other capabilities of the disclosed subject matter will be more fully understood after a review of the following figures, detailed description, and claims.

BRIEF DESCRIPTION OF THE FIGURES

These and other features will be more readily understood from the following detailed description taken in conjunction with the accompanying drawings, in which:

FIG. 7 illustrates an exemplary graphical user interface for displaying the distribution of data associated with sensors associated with a space in a building;

DETAILED DESCRIPTION

Figure 1:
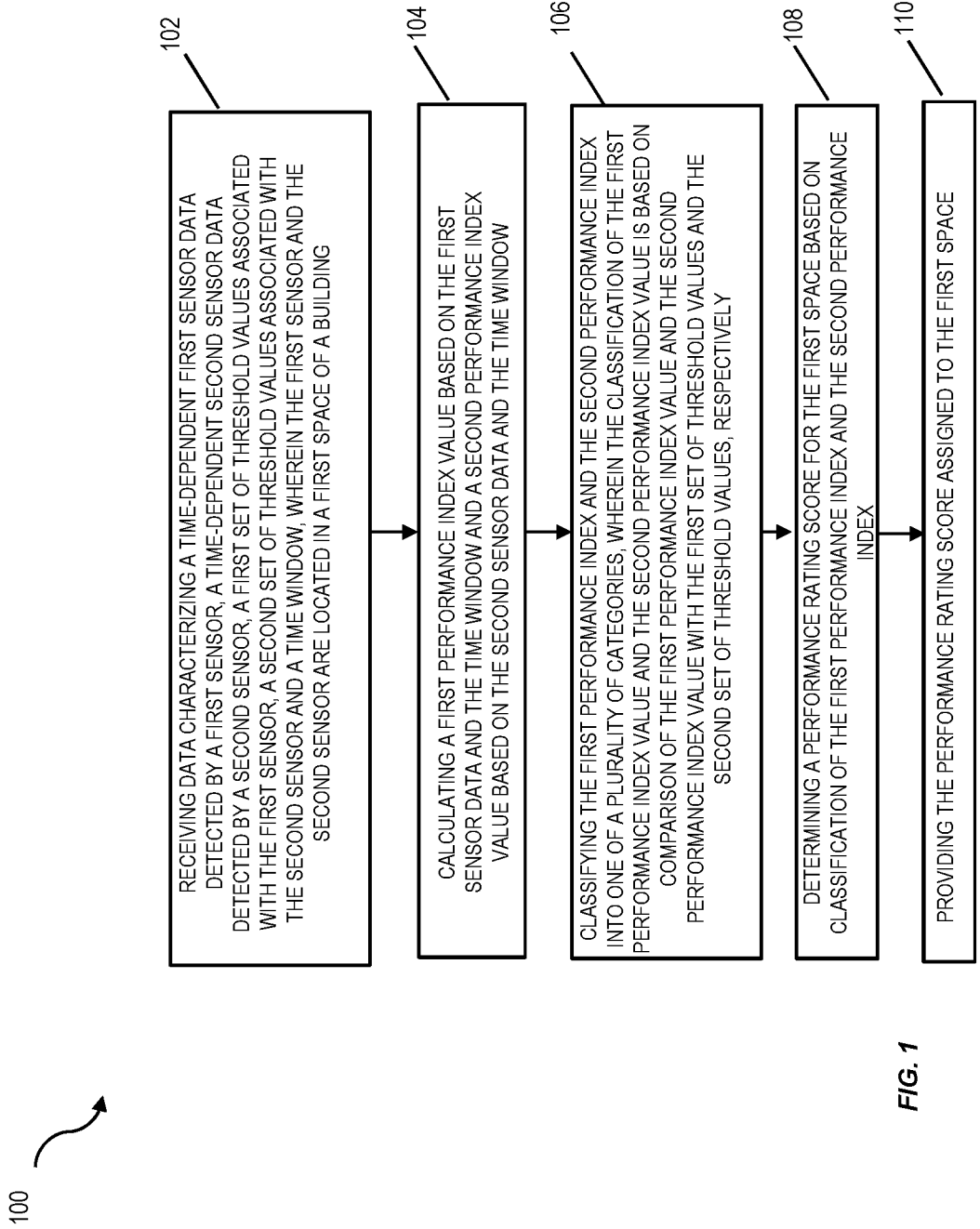
FIG. 1 is a flow chart of an exemplary method for assigning a health performance indicator category to a space in a building.

Indoor air quality (IAQ) of a building can impact the health and well-being of occupants of the building. The IAQ can depend on various indoor air factors associated with the building (e.g., $CO_2$ concentration, $PM_{2.5}$ concentration, temperature, humidity, concentration of volatile organic compounds (VOCs), radon concentration, etc.). These factors can be measured by installing sensors at various locations of the building. The sensors can measure the concentration of various factors that can then be monitored (e.g., to determine if the concentration is in an undesirable range). Additionally, it can be desirable to monitor the IAQ in real-time (e.g., throughout the day) in order to detect changes in the air quality of the building (e.g., time-dependent deterioration in the air quality of a building or a space therein).

Monitoring IAQ that depends on multiple indoor air factors (measured by multiple sensors) in real-time can be challenging (e.g., due to large amount of sensor data). In some implementations of the current subject matter, systems and methods for calculating a performance indicator of a building are described that provide an accurate description of the indoor air quality of the building based on comparing the instantaneous spot measurement from the sensor with predetermined thresholds (e.g., published thresholds). Additionally, by using predetermined thresholds, some implementations of the current subject matter may provide computational advantages over conventional systems that are inadequately equipped to process a large amount of sensor data. These approaches can account for several critical factors in determining human health risk, and therefore the overall rating or performance of the space and building. For example, these approaches can account for appropriate averaging times for each sensor and IAQ parameter, health-based thresholds based on those averaging times, a method for placing one or more sensors within a space, a method for determining whether any IAQ data points or datasets are unreliable, a method for scoring the performance of the space across the various IAQ parameters using the averaging times and health-based thresholds, a method for scoring the performance of the building across multiple sensors, and a method for using blockchain technology to create an immutable record for each parameter (including averaging time and threshold), for each space, and for the building, etc.

A building can be partitioned into multiple spaces. A space may be composed of a room, a collection of rooms, a floor, a whole building, or any portion thereof. Each space can include one or multiple sensors (e.g., $CO_2$ sensor, $PM_{2.5}$ sensor, humidity sensor, temperature sensor, volatile organic compound (VOC) sensor, etc.) that can monitor the air quality of the space. A sensor package composed of multiple sensors can be located within a space. A plurality of sensor packages each composed of multiple sensors can be located within a space.

Based on sensor data in a given space, a spatial performance indicator can be assigned to the space. The building health performance indicator can be assigned based on the spatial performance indicators associated with the different spaces in the building. Determining the building health performance indicator from spatial performance indicators can allow for determining spatial patterns in the indoor air quality of the building. Additionally, each spatial performance indicator can be calculated at various time instances (e.g., by averaging sensor data over a time window). This can allow for determining temporal patterns in the indoor air quality of individual spaces and the building.

Spatial and building health performance indicators can provide building operators actionable information to improve the comfort, health and work performance of occupants of a building. Unlike existing techniques for monitoring indoor air quality of buildings which may rely on techniques based on one-time spot measurement, spatial and building health performance indicators can help to identify spatial and temporal patterns in the air quality which can provide clues to the sources of air quality issues in the building. Real-time measurements may provide building operators with actionable information to improve undesirable (e.g., suboptimal) building conditions (e.g., even before occupants are affected). Moreover, real-time measurements help can building operators ensure that buildings are supporting occupant comfort, health, safety, and work performance which can boost employers' bottom lines through reducing employee absenteeism and improving productivity.

In some embodiments, a processor for a monitoring system may receive data from the placed sensors including data for determining performance indicators.

FIG. 1 is a flow chart of an exemplary method for assigning a performance indicator to a space in a building (or a spatial performance indicator). The spatial performance indicator can be indicative of the indoor air quality (IAQ) of the space. At step 102, data characterizing a time-dependent first sensor data detected by a first sensor (e.g., $CO_2$ sensor), and a time-dependent second sensor data detected by a second sensor (e.g., $PM_{2.5}$ sensor) can be received. The data can be received by a monitoring system configured to monitor the indoor air quality of the building. One or more sensors (e.g., first sensor, second sensor, etc.) or sensor packages (which contain sensors that measure various IAQ parameters packaged together in one device) can be positioned in a space of the building (e.g. a first space) to detect indoor air factors.

The raw sensor data from all sensors in a space can be combined with threshold values associated with the various sensor data (e.g., first sensor data, second sensor data, etc.) and a time window (e.g., averaging time). Therefore, each parameter in each sensor can be assigned a performance index based on the raw data combined with a computed score based on the averaging time and thresholds. The performance index values across IAQ parameters in a space are then scored to give a performance rating scores for the space for a suitable time window (e.g., day, week, month, year, and/or for all-time). The performance rating scores for each space in a building are then used to determine a building performance indicator for a suitable time window (e.g., that day, week, month, year, and/or for all-time).

In some embodiments, the systems and methods described herein may include a method for determining whether any sensor data (e.g., associated with different sensors) received at step 102 is unreliable. For example, in some embodiments, a method may perform data quality checks on IAQ datasets prior to assigning performance indicators. Data quality checks may include, but are not limited to, assessments of data completeness, outliers, and variability. For example, in some embodiments, assessments of data completeness may compare the amount of data collected by one or more sensors to an amount of data expected for individual parameters. Data completeness assessments may be performed for individual parameters and for all parameters combined. In some embodiments, data completeness assessments may also identify and remove duplicates in datasets. In some embodiments, data completeness assessments may also identify gaps in the data. Additionally, assessments of outliers may identify any measurements outside of sensor measuring ranges or any outside of expected ranges of values. Assessments of variability may include identification of periods when the variability in sensor measurements is lower than would be expected in a building under normal operating conditions.

Data quality checks may include one or more checks to determine data completeness. For example, the data set may be analyzed to determine if there are prolonged gaps in the data from any sensors or if the data is relatively complete overall. In this manner, the use of incomplete data sets, which may result in biased or unrepresentative analysis, is prevented. In some embodiments, data completeness may be determined on a timescale (i.e., 1 hour), and represented as a percentage of the sensors for a parameter which reported data at least once during the timescale for the time period. Data quality checks may also screen for duplicates. Duplicates may be indicative of problems with data recording or transmission. The inclusion of duplicates in the dataset may have led to misleading visual or statistical summaries, which can be avoided by performing data quality checks as described herein.

Data quality checks may also screen for sensors with data gaps for all parameters. Data gaps may be indicative of sensor malfunction, unstable power, and/or poor internet connectivity. Data gaps for larger than 10% of the time period may be flagged for intervention. In some embodiments, sensors with data gaps for individual parameters may be flagged. For example, in some embodiments, less than 10% of values should be reported as Not Applicable so that data quality is preserved and the dataset is representative of the monitored areas.

Data quality checks may also screen for sensors reporting values that fall outside of measurements ranges. These values may have reduced accuracy or may be prone to error. If a sensor frequently reports measurements outside its measurement range, the sensor may be flagged for calibration or replacement. Values may be considered outside the sensor measurement range if they are less than the sensor measurement range minimum or greater than or equal to the range maximum. Data from sensors with more than 1% of data outside the sensor measurement ranges in the time period may be represented visually. Data quality checks may also screen for sensors that report abnormally low variation. In general, indoor environmental quality parameters may vary naturally throughout the course of a day. In cases where specific parameters have abnormally low variation over the course of several days, a sensor may be malfunctioning thus resulting in low data quality.

Data quality checks may be associated with follow-up actions such as confirming that sensor power and connectivity are stable, confirming that sensors are properly calibrated, confirming that sensors are appropriately responding to changes in environmental conditions, confirming that the sensors are functional, confirming that connectivity for the sensors is functional, and the like.

At step 104, performance indices can be calculated for sensor data (e.g., associated with different sensors) received at step 102. For example, a first performance index can be calculated for the first sensor data and a second performance index can be calculated for the second sensor data. Determination of a performance index for the first sensor data can be based on selecting a portion of sensor data and calculating an index (e.g., based on the averaging time) associated with the selected sensor data. In some implementations, a first portion of the first sensor data that temporally spans from a first time to a second time (e.g., the first portion of the first sensor data was detected between the first time and the second time) can be selected. The duration of the first portion of the first sensor data corresponds to the time window (e.g., difference between the second time and the first time is the duration of the time window). Once the first portion of the first sensor data has been selected, a first performance index can be calculated by, for example, calculating an average of first portion of the first sensor data. These performance indices are continually computed, such that 'rolling averages' are calculated for each IAQ parameter in each space. In some embodiments, 'rolling averages' for each parameter may include various time windows. In some embodiments, 'rolling averages' for each parameter may include the same time window.

This process can be repeated for sensor data generated by different sensors in the first space of the building. For example, a second performance index can be calculated for a portion of a second sensor data generated by the second sensor located in the same space as the first sensor. The second sensor performance index can be calculated by selecting a portion of the second sensor data (e.g., based on the time window), and by calculating an average of the selected portion of the second sensor data.

In some implementations, multiple performance indices can be calculated for sensor data generated by a sensor. For example, a second portion of the first sensor data that temporally spans from a third time to a fourth time (e.g., the second portion of the first sensor data was detected between the third time and the fourth time) can be selected. The duration of the second portion of the first sensor data corresponds to the time window (e.g., difference between the fourth time and the third time is the duration of the time window). A performance index of the second portion of the first sensor data can be calculated by, for example, calculating an average of second portion of the first sensor data.

In some implementations, different portions of a sensor data (e.g., first portion and second portion of the first sensor data) can be temporally staggered. For example, the temporal extent of the first portion of the first sensor data may not overlap with the temporal extent of the second portion of the first sensor data. In some implementations, different portions of the sensor data used to calculate performance indices may temporally overlap.

For a given space in a building, multiple performance indices can be generated from different portions of sensor data from a sensor in the given space and/or from sensor data generated by different sensors in the given space. At step 106, the various performance indices calculated at step 104 can be classified into one of a plurality of categories (e.g., health optimized, excellent, action, alert, limit, etc.). The classification of the performance indices (e.g., first performance index, second performance index, etc.) is based on threshold values associated with each IAQ parameter. For example, sensor data from a first sensor (e.g., $CO_2$ sensor) can be associated with a first set of threshold values, and a second sensor (e.g., $PM_{2.5}$ sensor) can be associated with a second set of threshold values, and, when combined, an overall category is determined for the space.

A performance index can be classified into one of a plurality of performance indicators based on comparison of the performance index with the corresponding set of threshold values (e.g. threshold values associated with the sensor data from which the performance index is generated). In some implementations, the classifications for performance indices can include (e.g., in decreasing order of desirability) health optimized, excellent, action, alert and limit. For example, a performance index can be classified as a second performance indicator (e.g., excellent) if it has a value between a first threshold value and a second threshold value, can be classified as a third performance indicator (e.g., action) if it has a value between a second threshold value and a third threshold value, etc. In some implementations, the performance index can be classified as a given performance indicator based on a single comparison with a threshold value. For example, a performance index can be classified as health optimized if the performance index has a value below a first threshold value. Table 1 below provides exemplary threshold values for sensors configured to detect $CO_2$, $PM_{2.5}$, total volatile organic compounds (TVOC), radon, temperature/relative humidity (RH), and noise, respectively. Based on the threshold values, the performance index can be classified as having a performance indicator corresponding to one of health optimized, excellent, action, alert and limit.

The threshold values for the performance indices may be for IAQ parameters for health, including but not limited to, $CO_2$, TVOCs, $PM_{2.5}$, and/or radon. Additionally, threshold values for the categorization of performance indices may be for thermal parameters. Thermal parameters may include, but are not limited, to temperature and RH. Additional threshold values for the categorization of performance indices may be for noise. Threshold values for parameters may vary by application. For example, threshold values for commercial office applications may be different than for residential applications or for industrial applications.

For example, Table 1 illustrates threshold values for a commercial office application. As shown, threshold values may be provided for a variety of performance indices including $CO_2$, $PM_{2.5}$, TVOC, radon temperature/relative humidity, and noise. Relative humidity may be measured based on $RH_{out-x}$, where x=1, 6, or 11, which is x less than the RH that a parcel of outdoor air would have if its temperature was changed from the outdoor temperature at a given time to the indoor temperature at the same time without changing the water content of the air.

TABLE 1

| | $CO_2$ (ppm) | $PM_{2.5}$ (ug/m³) | TVOC (ppb) | Radon (pCi/L) | Temperature (F)/RH (%) | Noise (dBA) |
|---|---|---|---|---|---|---|
| Health optimized | <800 | <5 | <300 | <0.4 | 70 < Temp < 76 & 30 < RH < 60 | <60 |
| Excellent | <1000 | <15 | <1000 | <1.3 | 68 < Temp ≤ 70 or 76 ≤ Temp < 78 & $RH_{out-1}$ < RH ≤ 30 or 60 ≤ RH < 65 | <70 |
| Action | <1500 | <35 | <2000 | <2 | 67 < Temp ≤ 68 or 78 ≤ Temp < 80 & $RH_{out-6}$ < RH ≤ RHout-1 or 65 ≤ RH < 70 | <75 |
| Alert | <2500 | <50 | <3000 | <4 | 66 < Temp ≤ 67 or 80 ≤ Temp < 82 & $RH_{out-11}$ < RH ≤ $RH_{out-6}$ or 70 ≤ RH < 80 | <80 |
| Limit | ≥2500 | ≥50 | ≥3000 | ≥4 | Temp ≤ 66 or Temp ≥ 82 & ≤ $RH_{out-11}$ RH ≥ 80 | ≥80 |

In some embodiments, in addition to classifying performance indices into the different performance indices (e.g., from different sensors), each sensor in a given space can be assigned a performance rating score.

For example, if at least 85% of the computed indices over a certain period of time fall within the top two categories (i.e., health optimized and excellent), and at least 5000 of the computed indices are in the top category (i.e., health optimized), the space corresponding to the different sensors may have a performance rating score of "health optimized."

In another example, if at least 85% of the computed indices over a certain period of time fall within the top two categories, and less than 50% of the computed indices are in the top category (health optimized), the space may have a performance rating score of "excellent".

In yet another example, if at least 75% but less than 85% of the computed indices over a certain period of time are in the top two categories, the space may have a performance rating score of "excellent".

In another example, if less than 75% of the computed indices over a certain period of time are in the top two categories, the space may have a performance rating score of "conventional".

In this manner, the disclosed systems and methods may score spaces within building.

In addition, each space may be tagged with the number of indices that fall into the 'action', 'alert', and 'limit' categories over a certain period of time. For example, a space might be labeled "excellent" with two "actions" for the week, as a means of notifying the building owner/operator that the space is performing well, but there are specific areas and times that might need attention and corrective action.

In some embodiments, the performance rating score may be composed of any number of scores. For example, the performance rating score may be composed of a first score and a second score and a third score. The first score of the performance rating score may correspond to IAQ parameters associated with heath that are determined separately from a second score that corresponds to one or more thermal parameters. The third score may also be determined separately and may correspond to noise. For example, a first score corresponding to IAQ parameters associated with health may be based on a score computed based on a thresholding of IAQ parameters including, but not necessarily limited to, $CO_2$, TVOCs, $PM_{2.5}$, and/or radon. For example, a second score corresponding to temperature and RH may be determined based on a thresholding of temperature and RH together. For example, a third score corresponding to noise may be determined based on a thresholding of noise.

At step 108, performance rating score can be assigned to a space in the building (e.g., the first space that includes the first sensor and the second sensor). The assignment can be based on the determined performance rating scores of the sensors in the space. As described above, the classification of the sensors in the space is based on the classification of performance indices associated with the sensors (e.g., first performance index, second performance index, third performance index etc.) performed at step 106. In some implementations, the space is assigned the performance rating score corresponding to the worst performing sensor in the space. For example, if the first sensor in the space is scored as action at a specific time and the second sensor is scored as alert at the same time, the space may be assigned a performance rating score of alert.

In some implementations, the performance rating score can be assigned to the space (e.g., the first space) based on the distribution of the performance indicators assigned to the performance indices from sensor data generated by sensors.

In some implementations, a building health performance indicator can be determined based on the performance indicators or performance rating scores assigned to spaces in the building. For example, a building may obtain a building health performance indicator ranging from optimized, excellent, action, alert, or limit, based on the percentage of spaces receiving performance rating scores of same classification. Buildings may be scored in an analogous manner to how individual sensors are scored. For example, the raw data may be used to generate rolling or time-weighted averages which are then classified into bins. In some embodiments a building score may be assigned based on how all the rolling or time-weighted averages from all the sensors in the building compare to the thresholds using the same cutoffs used for an individual sensor. In some embodiments, some sensors in the building may be weighted differently from other sensors in the building.

At step 110, the performance indicator(s) and performance rating score assigned to the first space can be provided. For example, the performance indicator assigned to the first space can be presented in a graphical user interface (GUI), such as FIG. 2. Performance indicators may also be presented in visualizations including, but not limited to, boxplots, timeseries plots, or scatterplots each of which may be generated for a sensor, floor, or building. In some embodiments, performance indicator(s) and performance rating scores can be provided to a user via an application programming interface (API) or the like. Visualizations may be incorporated into reports or displays.

At step 112, the performance indicator(s) and performance rating scores can be used for adjusting sensor placement within the space. For example, data from the performance indicator(s) and performance rating scores can be incorporated into model in order to direct follow up actions after sensor data from a space indicate that the space has a performance rating score indicative of exceeding action, alert, or limit thresholds. In some embodiments, a model may be used to check whether the current sensor density is sufficient to determine whether the exceedance is locally contained and, if it is not sufficient, the model could also be used to recommend where additional sensors be placed in the space. In cases where it is confirmed that sensor density is sufficient, comparison of data from the sensor with the exceedance with data from nearby sensors can help determine follow-up actions (e.g., if the sensor needs replaced because it was malfunctioning, if there are spatial or temporal patterns indicating how IAQ improvements could be achieved).

In some embodiments, data characterizing a time-dependent first sensor data detected by a first sensor, a time-dependent second sensor data detected by a second sensor, and a time-dependent third sensor data detected by a third sensor may be received. Additionally, data characterizing a set of first threshold values associated with the first sensor, a set of second threshold values associated with the second sensor, and a set of third threshold values associated with the third sensor may also be received. Data characterizing a time window may be received. In some embodiments, the first sensor, the second sensor, and the third sensor are located in a first space of a building. A first performance index can be calculated based on the first sensor data and the time window, a second performance index can be calculated based on the second sensor data and the time window, and a third performance index can be calculated based on the third sensor data and the time window. Each of the first performance index, the second performance index and the third performance index can be classified into one of a plurality of performance indicators, where the classification of the first performance index, the second performance index, and the third performance index is based on comparison of the first performance index, the second performance index, and the third performance index with the first set of threshold values, the second set of threshold values, and the third set of threshold values respectively. A performance rating score can be determined for the first space by scoring the classification of first performance index, the second performance index, and the third performance index within the plurality of performance indicators. The performance rating score assigned to the first space can then be provided or displayed in a graphical user interface, application user interface, report or the like.

Figure 2:
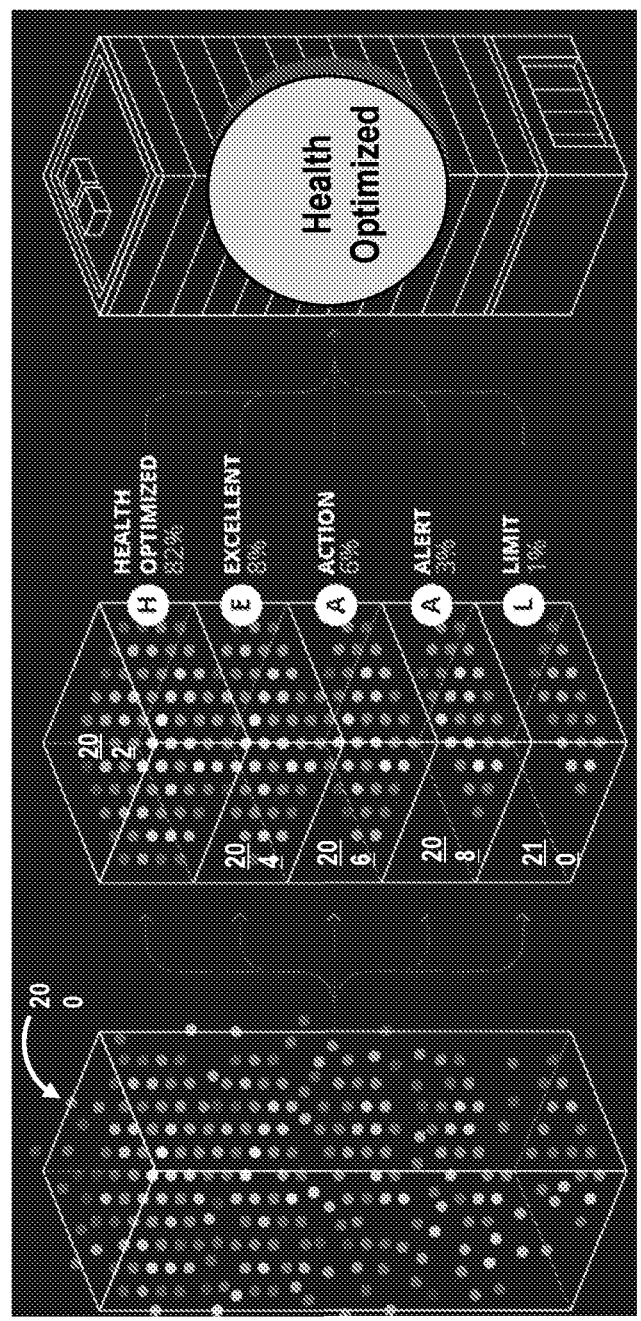
FIG. 2 illustrates an exemplary graphical user interface for displaying the distribution of performance indices associated with a space in a building.

FIG. 2 illustrates an exemplary graphical user interface 200 for displaying the distribution of performance indices (associated with sensor data from a space) over the various performance indicators. Other visualizations including unique boxplots, timeseries plots, or scatter plots may also be used to visualize performance indices. Health performance indicators (which are representative of sensor data averaged over one or more averaging times/time windows) are displayed in the far left image 200. Raw indoor environmental quality data can be collected by sensors in a building and aggregated into health performance indicators in time-weighted averages (e.g., 1-hour and 8-hour averages) covering the building's occupied hours as displayed in the far left image 200. These health performance indicators can be sorted into the appropriate bins and response categories (middle image). Sorting the health performance indicators may be based on comparing the averages against parameter-specific thresholds. Based on the sorting, the scoring algorithm can compute a performance rating score for the space (right image), and then a score for the entire building (e.g., a building performance indicator). For example, the scoring algorithms may provide a building's indoor air quality, thermal, and/or noise scores, as well as action, alert and limit notifications.

Each health performance indicator can be represented by a graphical object (e.g., by an image of a circle, marble, or ball), and the performance indicators are then visually represented being sorted into different categories (e.g., a bin, or graphical depiction of a floor of a building). Depending upon the classification of the performance index, the graphical object associated with the performance index is placed in one of the five bins 202-210. For example, a health optimized performance indicator is represented by a first bin 202, an excellent performance indicator is represented by a second bin 204, an action performance indicator is represented by a third bin 206, an alert performance indicator is represented by a fourth bin 208, and a limit performance indicator is represented by a fifth bin 210.

In some implementations, the rendering of the graphical objects associated with performance indices in the GUI 200 can be dynamic. For example, a graphical object can first appear in a first region 200 of the GUI 200 and then traverse from the first region to one of the five bins 202-210. After the graphical object arrives in a given bin, it may continue to be subsequently displayed. With the passage of time as more sensor data is collected, new graphical objects (e.g., corresponding to new performance indices) are generated and placed in one of the bins 202-210.

In some implementations, a graphical user interface may be configured to display and render graphical objects associated with performance indices or performance rating scores over various time frames (e.g., all-time, past month, past week, past day).

Graphical objects may be included in a graphical user interface, integrated into an application programming interface, or used to generate reports that may be provided to a user in any suitable form (e.g., document reports, graphical display).

Figure 3:
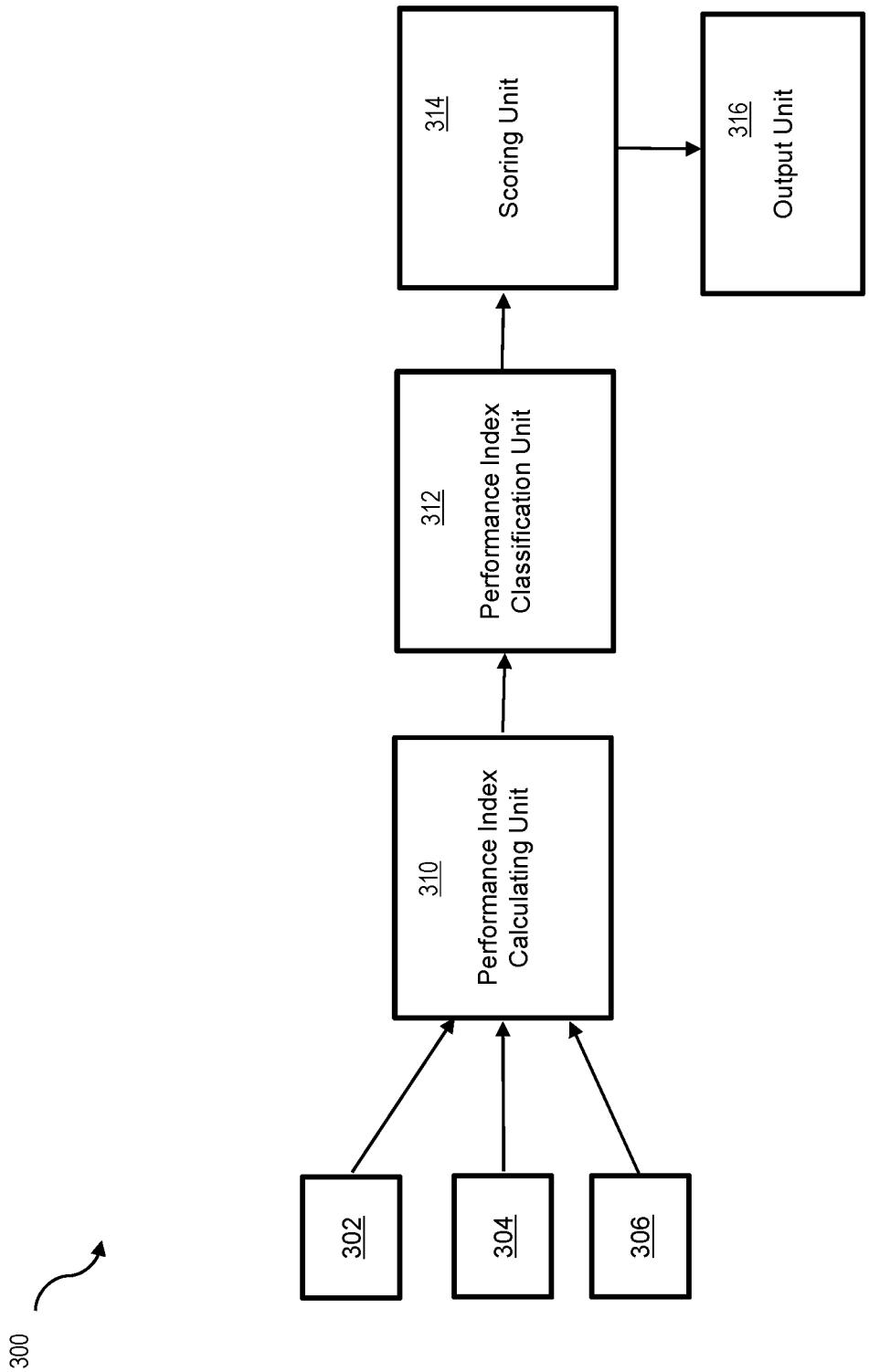
FIG. 3 illustrates an exemplary spatial monitoring system for monitoring indoor air factors of a space.

FIG. 3 illustrates an exemplary spatial monitoring system for monitoring indoor air factors of a space. The spatial monitoring system can include sensors 302-306 that can detect air factors in the space.

Embodiments of the present disclosure may include a method of positioning the sensors 302-306 within a spatial monitoring system. In some embodiments, one or more sensors 302-306 or sensor packages may be distributed within a space at various locations. For real-time IAQ data to adequately characterize an indoor space, a sufficient number of sensors must be placed at appropriate locations within large open indoor spaces (e.g., open offices, large meeting rooms, cafeterias, etc.). A model may receive environment data and generate recommendations for the number of required sensors, sensor types, and the location of their placement within the space. Environment data may include information about specific air parameters of interest (e.g., $CO_2$, $PM_{2.5}$). Environment data may include information about the space where sensors will be placed (e.g., ventilation, infiltration, and recirculation rates; heating, ventilation and air conditioning (HVAC) filter type; airflow within the space; and the space dimensions). In some embodiments, if environmental data corresponding to the characteristics of the space are unknown, default parameters for the environmental data may be used. Additionally, the environment data may include floor plans for the space.

The model may be used to determine appropriate positions for a sensor or sensor package within a space. Using received environmental data, the model may determine a zone of possible placements for each sensor or sensor package. The zone of possible placements may be based on a calculation how far away a sensor could be placed from a source of the air parameter of interest while still being able to measure elevated parameter levels at a certain timepoint or ever (i.e., before it is removed/diluted). Although source concentrations and elevated target levels measured by the sensor can be customized, in some embodiments the method may use default parameters corresponding to the limit threshold concentrations for each sensor as the source concentrations and the action threshold concentrations for each air parameter of interest to indicate an elevated concentration.

In some embodiments, the model may recommend that sensors be placed throughout a space such that a sustained source at a concentration equal to the limit threshold within the area covered by each sensor would be detected (i.e., would reach an action threshold) by a sensor within a certain amount of time.

In some embodiments, the model may also be used to direct follow up actions after sensor data from a space has exceeded action, alert, or limit thresholds. In such an embodiment, the model can be used to check whether the current sensor density is sufficient to determine whether the exceedance is locally contained and, if it is not sufficient, the model could also be used to recommend where additional sensors be placed in the space. In cases where it is confirmed that sensor density is sufficient, comparison of data from the sensor with the exceedance with data from nearby sensors can help determine follow-up actions. Examples of follow-up actions may include recommendations that a sensor needs replacement, or adjustments in positioning. Other examples of follow-up actions include spatial or temporal patterns which indicate how indoor air quality improvements could be achieved.

The sensors 302-306 can transmit sensor data representative of the detected air factors to a performance index calculating unit 310 that can calculate performance indices associated with the sensor data (e.g., as described in step 104 of FIG. 1). The performance indices generated by the performance index calculating unit 310 can be provided to the performance index classification unit 312 that can classify the performance indices as different performance indicators (e.g., as described in step 106 of FIG. 1). The classified performance indices can be provided to the scoring unit 314 that can assign performance indicators and space performance rating scores to the space (e.g., as described in step 108). In some implementations, information associated with one or more of the health performance indicators of the space, health performance indices, and health performance indicators associated with the performance indices can be provided to an output unit 316. The output unit 316 can display the aforementioned information in a graphical user interface (e.g., graphical user interface 200). In some implementations, the output unit 316 can transmit or store the information in a database. In some embodiments, the output unit 316 may provide the information to a model.

In some implementations, information associated with one or more of the performance indices, health performance indicators, space performance rating scores, and building performance indicators can be stored in a blockchain. For example, a health performance index and the corresponding health performance indicator can be assigned a block in a blockchain. The block can be associated with a space (e.g., the health performance index is calculated from the sensor data generated by the sensor located in the space), a building that includes the space and an averaging time used to calculate the health performance index. The blockchain can allow for creation of an immutable record of the various health performance indicators and health performance indices generated in the spaces of a building. In some implementations, information associated with the performance of a building can be shared (e.g., between owner of the building and insurance companies) by sharing the blockchain.

In some implementations, the aforementioned information (e.g., the health performance indicators of the space, health performance indices, health performance indicators associated with the performance indices, etc.) can be provided to a building automation systems (BAS) or building management systems (BMS) to instantaneously adjust the building systems based on the computed performance indicators for the space and building. After the health performance indicators are created, that data associated with the health performance indicator can be provided to the BAS/BMS for a corrective action (e.g., instantaneous corrective action). For example, if high $CO_2$ is detected and categorized as an 'alert', the building would automatically adjust the outdoor air damper to bring in more outdoor air.

Figure 4:
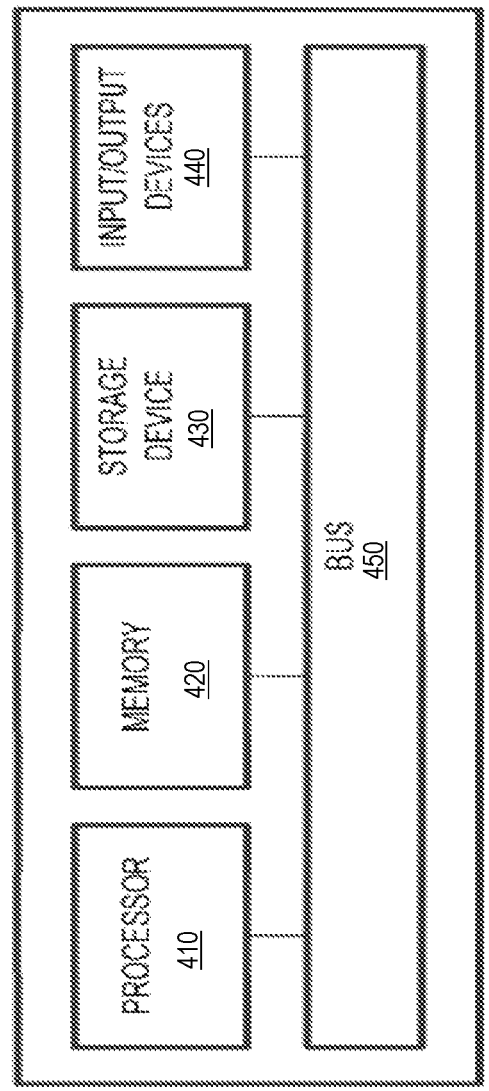
FIG. 4 illustrates a block diagram illustrating an example of a computing system, in accordance with some example embodiments.
Figure 4:
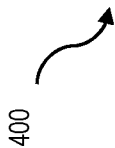

FIG. 4 illustrates an exemplary computing system 400 configured to execute the data flow described in FIG. 1. The computing system 400 can include a processor 410, a memory 420, a storage device 430, and input/output devices 440. The processor 410, the memory 420, the storage device 430, and the input/output devices 440 can be interconnected via a system bus 450. The processor 410 is capable of processing instructions for execution within the computing system 400. Such executed instructions can implement one or more steps for calculating and classifying performance indices, assigning a performance indicator to a space/building, etc. In some example embodiments, the processor 410 can be a single-threaded processor. Alternately, the processor 410 can be a multi-threaded processor. The processor 410 is capable of processing instructions stored in the memory 420 and/or on the storage device 430.

The memory 420 is a computer readable medium such as volatile or non-volatile that stores information within the computing system 400. The memory 420 can store performance indices, performance indicators, etc. The storage device 430 is capable of providing persistent storage for the computing system 400. The storage device 430 can be a cloud-based storage system (e.g., AWS), floppy disk device, a hard disk device, an optical disk device, a tape device, a solid state drive, and/or other suitable persistent storage means. The input/output device 440 provides input/output operations for the computing system 400. In some example embodiments, the input/output device 440 includes a keyboard and/or pointing device. In various implementations, the input/output device 440 includes a display unit for displaying graphical user interfaces. In some implementations, the GUI 300 can be displayed in a display of the input/output device 440.

FIGS. 5-22 provide illustrations of an implementation of the claimed subject matter, where sensor data, parameters, and metrics derived therefrom are provided to a user via report, graphical user interface, application user interface, or the like.

The implementation illustrated in FIGS. 5-22 illustrates a commercial space embedded with real-time sensors configured to gather IAQ data. IAQ parameters including $CO_2$, $PM_{2.5}$, and TVOCs were determined based on the gathered IAQ data, and rolling averages for these IAQ parameters were compared against the threshold ranges to determine an IAQ score.

Key metrics may be determined and displayed to a user in a report, graphical user interface, application user interface and the like. Examples of key metrics include, IAQ Score, TRH Score, Noise Score, % of $CO_2$ data in Health Optimized or Excellent threshold ranges, % of $PM_{2.5}$ data in Health Optimized or Excellent threshold ranges, % of TVOC data in Health Optimized or Excellent threshold ranges, and the number or names of floors with conventional IAQ scores. Key metrics may also indicate sensors associated with values that are consistently outside of a target range. For example, key metrics may include a listing of sensors with elevated TVOC values, elevated $PM_{2.5}$ values, elevated temperatures, elevated noise levels, and the like. Data completeness, outliers, variability metrics for sensor data may also be provided. Data sets, key metrics, performance indicators, and the like may be provided to a user via a user interface.

In some implementations of the claimed subject matter, users may be presented with sensor data, parameter data, and metrics derived therefrom in a graphical user interface that is integrated into a user application such as a website, computer program, mobile application, and the like. The graphical user interface can be configured to be interactive and dynamic. For example, the graphical user interface can be configured to receive user input that generates user input data. The user input data may indicate a selection from the user as to what visualizations they would like to see. For example, a portion of a display screen provided to a user may be updated with a graphical user interface that shows sensor data for one or a set of parameters, one floor or a collection of floors, for a particular time range, and the like. A user may navigate through data provided as a summary to view specific subgroups of the visualization data. Upon selecting a particular subgroup of the visualization, the user may be presented with a more detailed level of data corresponding to the selected subgroup in a second visualization. In some embodiments, the user may be able to provide user input to adjust the timescales and parameters for the performance index values, performance rating scores, or the like.

Figure 5:
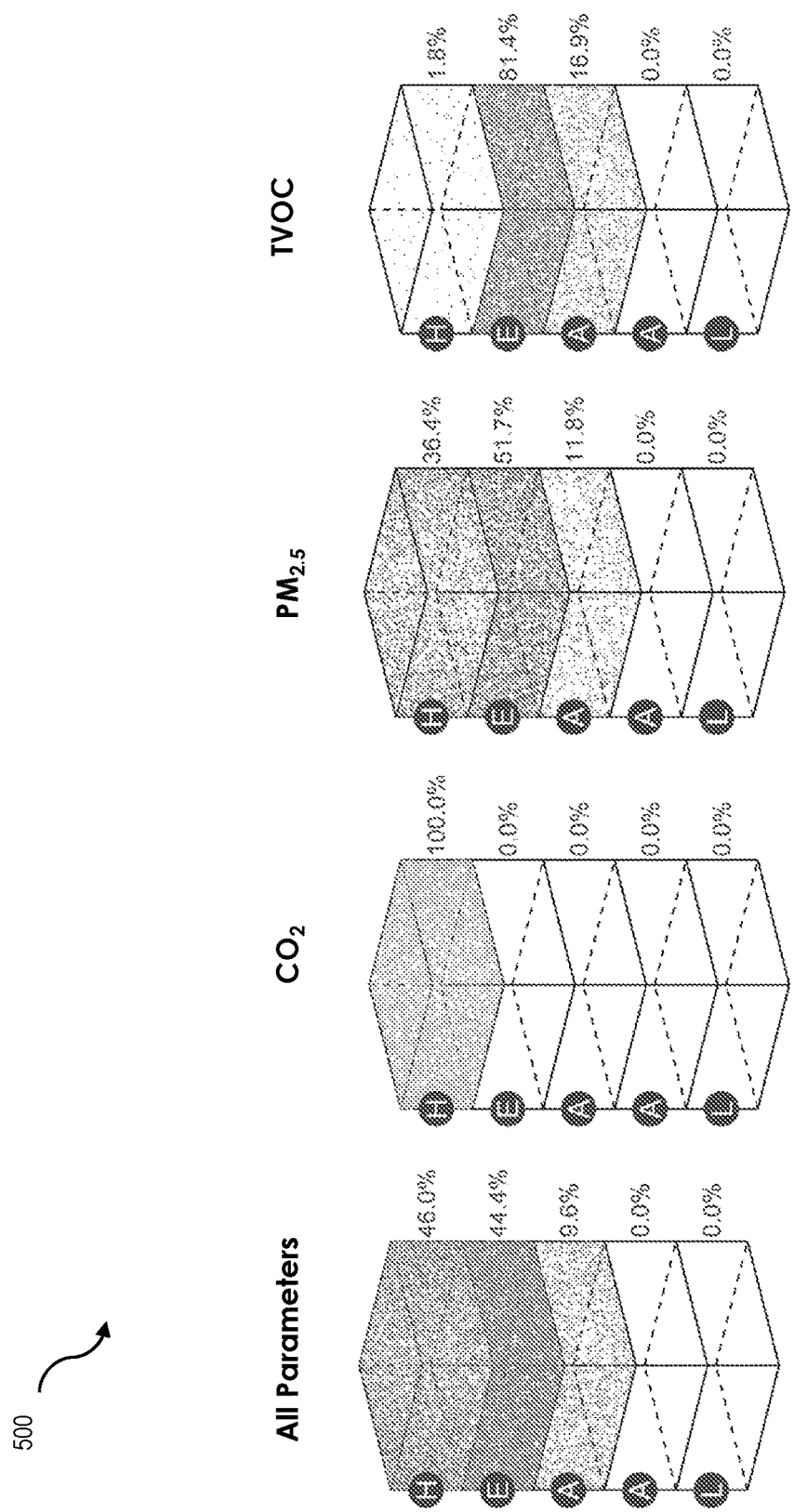
FIG. 5 illustrates an exemplary graphical user interface for displaying the distribution of performance indices associated with a space in a building.

FIG. 5 provides an example of an IAQ summary plot that is configured to display data to a user. FIG. 5 illustrates an exemplary graphical user interface 500 for displaying the distribution of performance indices (associated with sensor data from a space) over the various performance indicators. Each tier of the plot may represent one of the threshold bins. Each point in the plot may represent a rolling average of cleaned concentration data of one IAQ parameter. Rolling averages may be calculated over any suitable time period, including for example, 1-hour, 8-hour, 24-hours, and the like. For example, the point may represent a 1-hour or 8-hour rolling average of cleaned concentration data of one IAQ parameter during typical occupied hours. Percentages to the right of the plot may represent the percent of cleaned concentration data during typical occupied hours that fall in each threshold bin. As shown in FIG. 5, in the left most plot, an overlay across all the parameters may be visualized. Alternatively or additionally, summary plots for each IAQ parameter may be determined.

Figure 6:
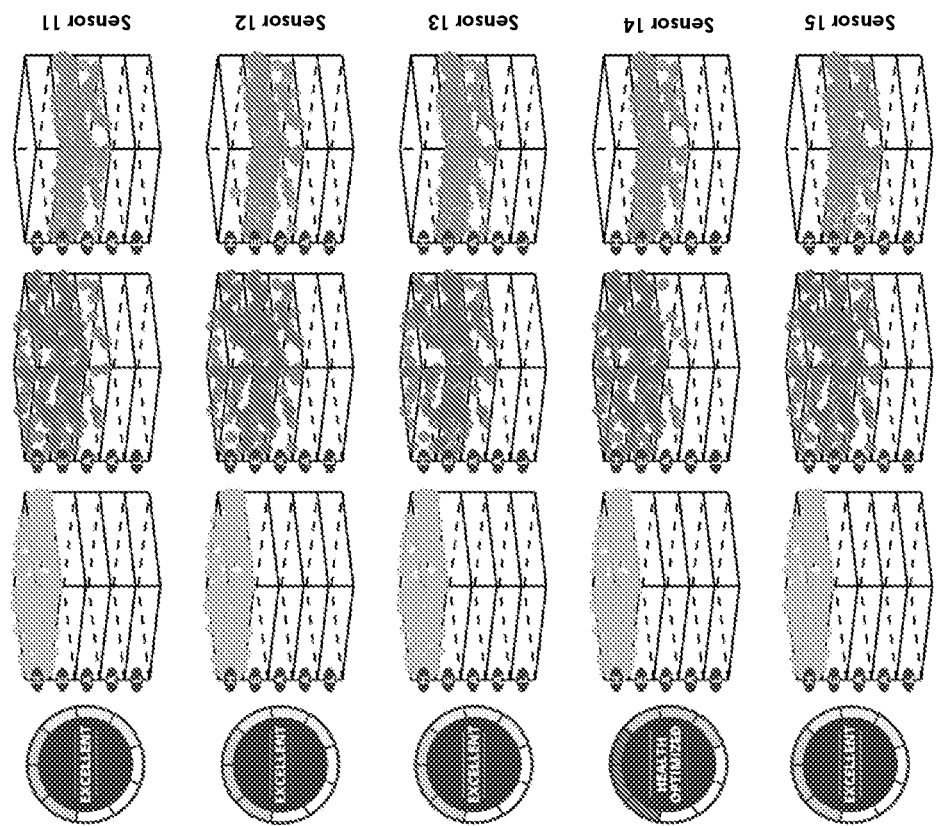
FIG. 6 illustrates an exemplary graphical user interface for displaying the distribution of performance indices associated with a space (i.e., a floor) in a building.
Figure 6:
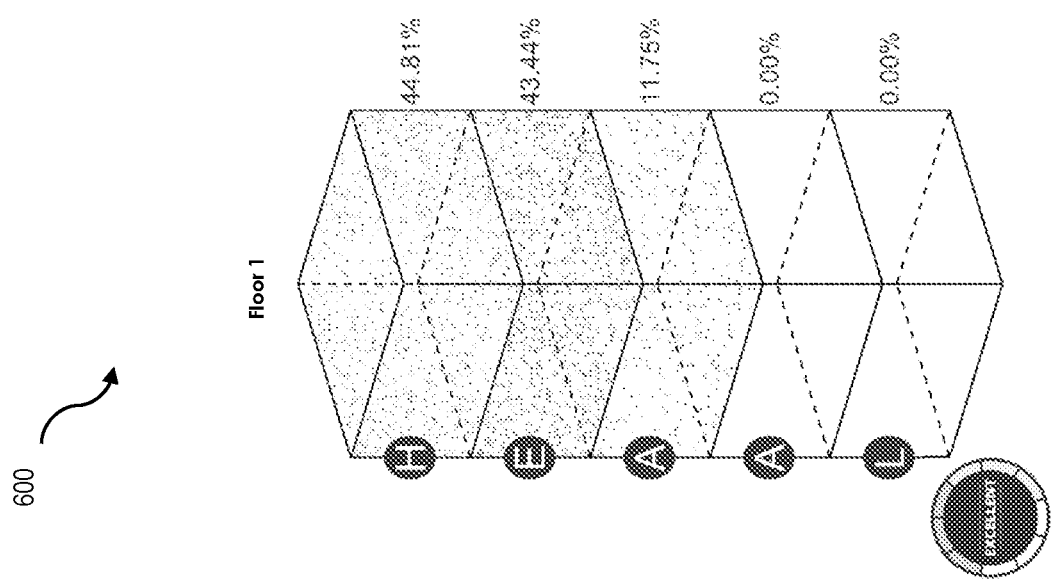

In some embodiments, the reports shown in FIG. 5 may be generated for each floor of a commercial space in which the described systems and methods are implemented. For example, FIG. 6 provides an example of an IAQ summary plot generated across a plurality of different floors in a commercial building. In some embodiments, the report may provide a summary of sensors, or floors that require an alert or alarm. As shown, a summary across all parameters for Floor one may be provided in the left-most plot of FIG. 6. Additionally, the graphical interface may provide a summary by sensor as shown in the right-side plots of FIG. 6. For example, a graphical representation of the overall score such as a badge can be displayed. In some embodiments, the graphical representation can be generated for each floor as well as for each sensor. In some embodiments, the badges may display text such as "Health Optimized" or "Excellent" and be color-coded when displayed to a user.

In some embodiments, the graphical user interface can be used to identify sensors that indicate IAQ issues. For example, a user may first be presented with data corresponding to all parameters such as was shown in FIG. 5. A user may then select a particular parameter (i.e., TVOC) for further review, and be presented with a visualization corresponding to the left-panel of FIG. 6. The user may then select a particular sensor affiliated with the selected parameter (i.e., sensors 11-15) for further review, as illustrated in the right-panel of FIG. 6.

Figure 7:
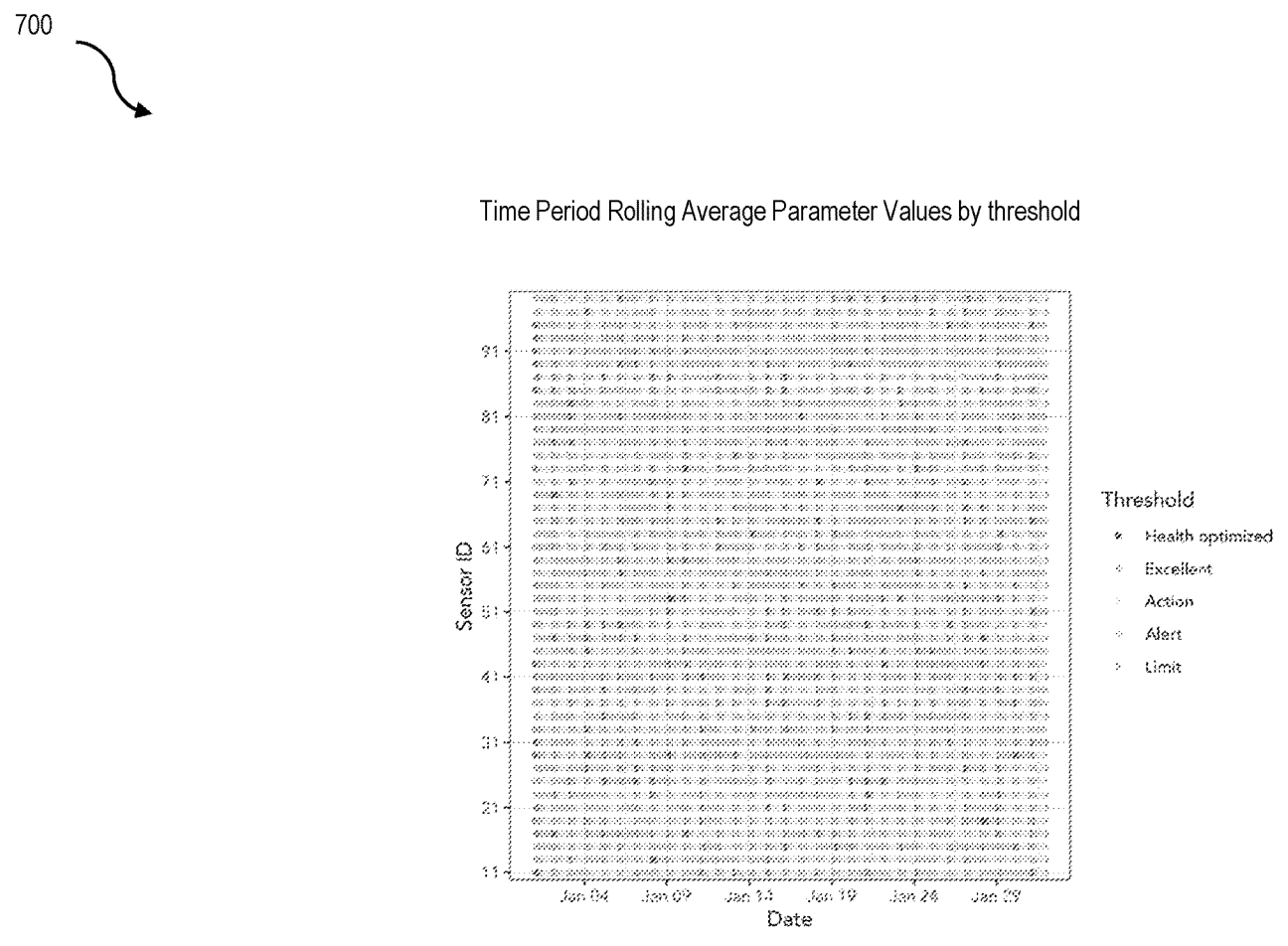

FIG. 7 provides an example of an IAQ map 700, which provides a graphical representation of the sensor data for a single parameter as compared to thresholds for a whole building over a time period. As shown, data for each date in the time (x-axis) can be plotted for each sensor (y-axis). Each data point in the IAQ map 700 can be assigned a different color, icon, or the like, based on the threshold range where the data point falls. Accordingly, the IAQ map 700 may provide a summary of data from all sensors for all time (i.e., typically occupied and unoccupied hours) in a building for a single IAQ parameter over the wholetime period for which a visual is generated. Each point may represent a rolling average concentration of the parameter shown. The IAQ map 700 may provide a user with a visual representation in trends in the data over space and time, allowing a user to quickly located sensors that may warrant investigation. IAQ maps can be generated for any parameter, including but not limited to, $CO_2$, $PM_{2.5}$, TVOC, noise, and the like. In some embodiments, the time period for which summary data is provided may be provided by a user, and may correspond to an entire reporting time, occupied hours only, unoccupied hours only, or the like.

Figure 8:
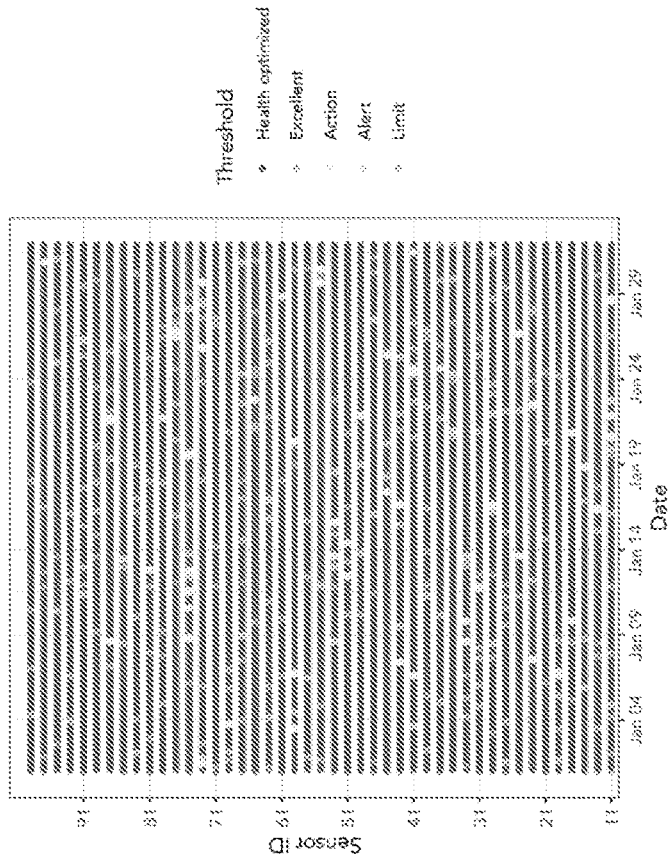
FIG. 8 illustrates an exemplary graphical user interface for displaying the distribution of data associated with sensors associated with a space in a building.

FIG. 8 provides an example of an IAQ map 800 of 1-hour rolling average $CO_2$ concentrations, which provides a graphical representation of $CO_2$ 1-hour rolling averages over the reporting period. As shown, in an implementation where the systems and methods described herein were deployed in a commercial building, the IAQ map 800 may show $CO_2$ 1-hour rolling averages in the Health optimized, Excellent, Action, Alert, and Limit ranges for a subset of sensors.

Figure 9:
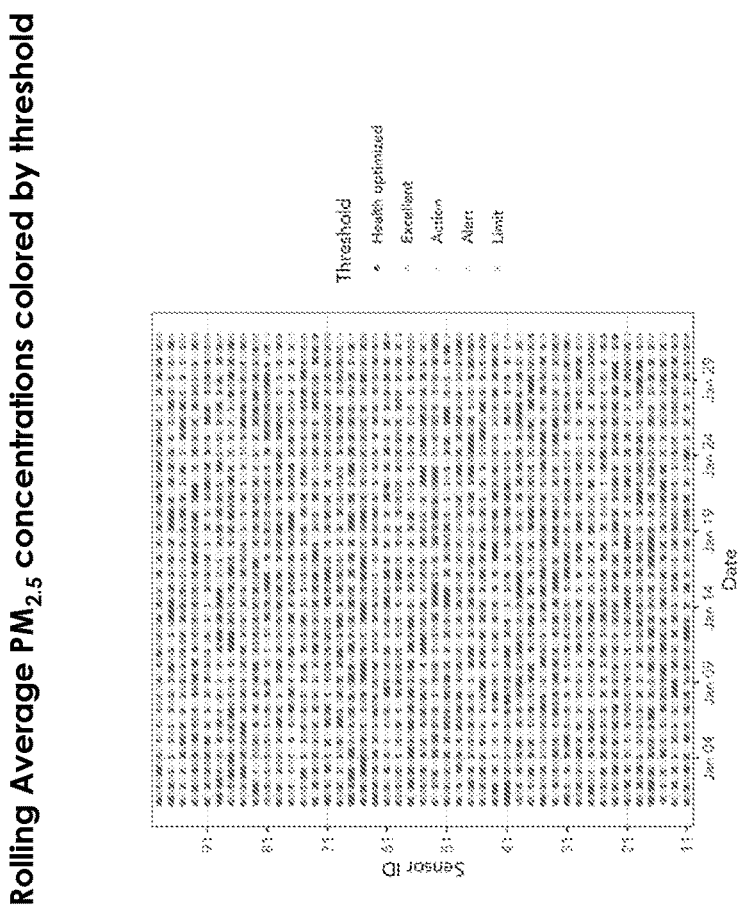
FIG. 9 illustrates an exemplary graphical user interface for displaying the distribution of data associated with sensors associated with a space in a building.

FIG. 9 provides an example of an IAQ map 900 of 1-hour rolling average $PM_{2.5}$ concentrations, which provides a graphical representation of $PM_{2.5}$ in 1-hour rolling averages over the reporting period. Accordingly, a user may identify a sensor at issue based on the visual representation and perform investigations into what the sensor determined as action or alert levels.

Figure 10:
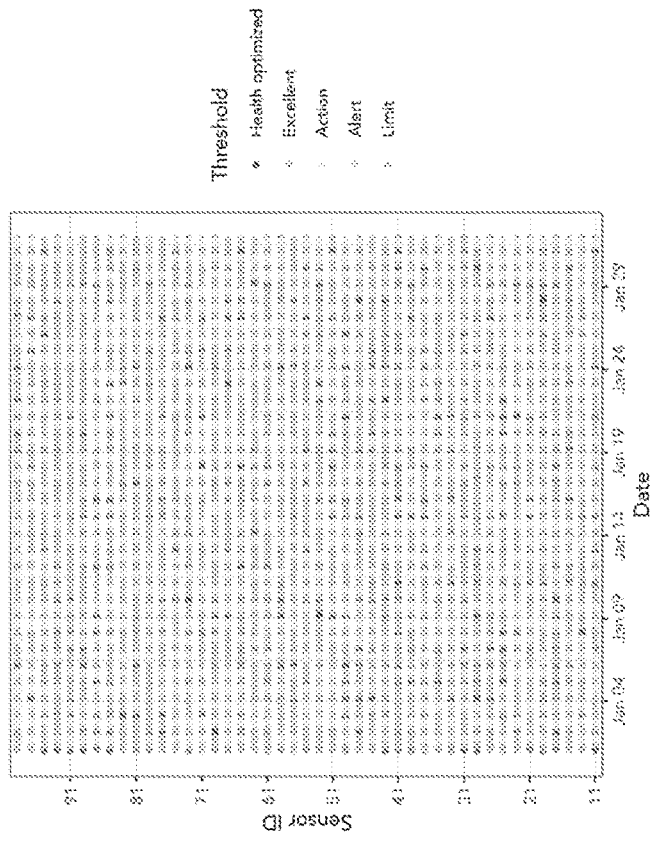
FIG. 10 illustrates an exemplary graphical user interface for displaying the distribution of data associated with sensors associated with a space in a building.

FIG. 10 provides an example of an IAQ map 1000 of 1-hour Rolling Average TVOC concentrations, which provides a graphical representation of TVOC in 1-hour rolling averages over the reporting period.

Figure 11:
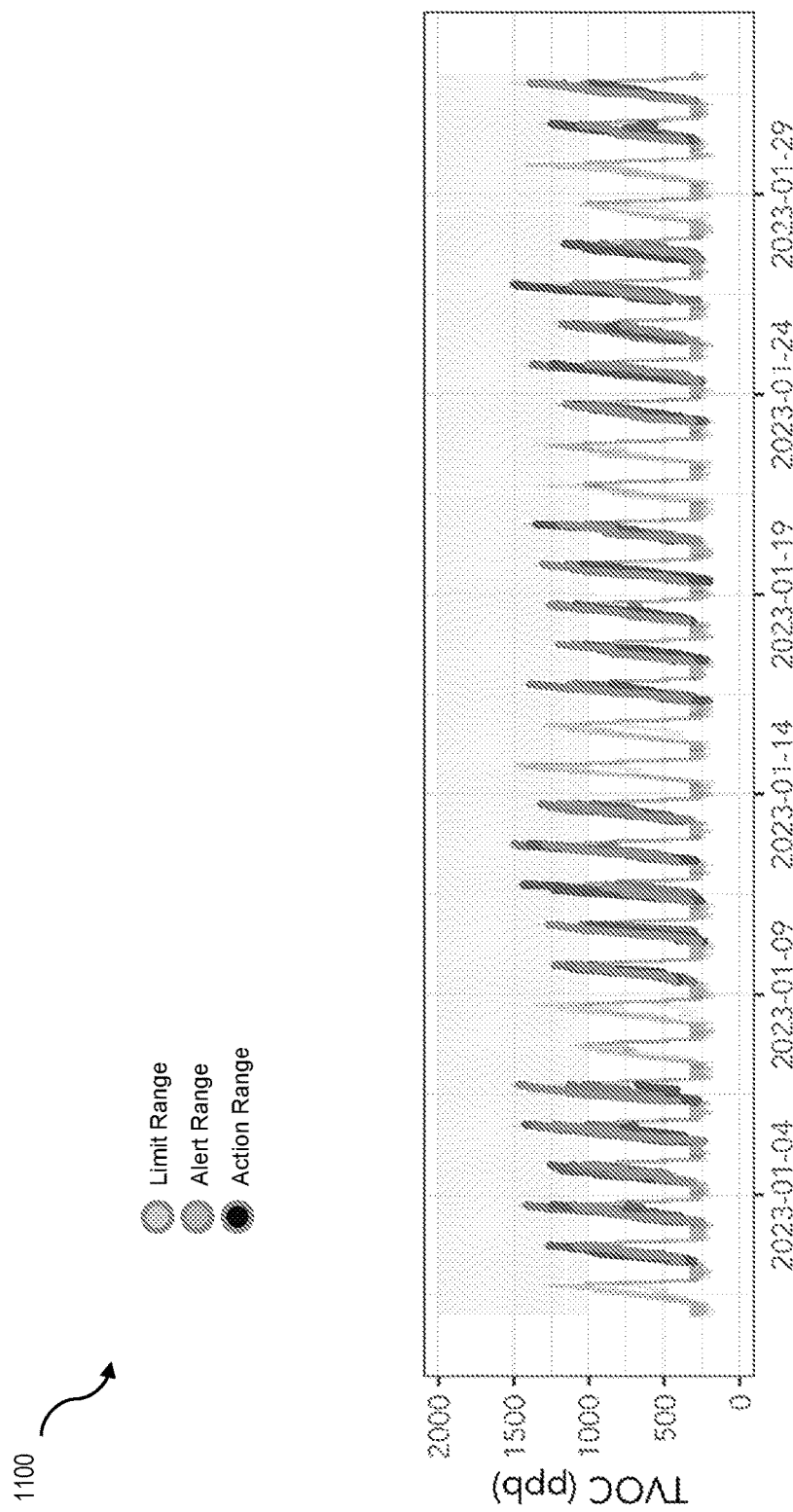
FIG. 11 illustrates an exemplary graphical user interface for displaying the distribution of data over time associated with sensors associated with a space in a building.

FIG. 11 provides an example of a visualization for a timeseries 1100 in accordance with some embodiments of the present disclosure. As illustrated in FIG. 11, data for a particular set of sensors corresponding to a parameter may be plotted on the y-axis across a plurality of dates on the x-axis. The concentration for a specific parameter plotted on the y-axis may be scaled based on the maximum concentration of that parameter in the data. Measurements from each sensor for the same IAQ parameter may be plotted. A graphical representation of cleaned raw data for all time may be displayed under lines that demonstrate rolling averages of the cleaned raw data. Bands identifying limit, action, and alert ranges may be overlaid upon the data. The timeseries visualization 1100 may convey patterns in measurements of an individual parameter by all sensors on a single floor over the reporting period. In particular, FIG. 11 provides a visualization for a timeseries 1100 of TVOC over time, and provides a graphical illustration of when parameter data is determined to be above certain thresholds.

Figure 12:
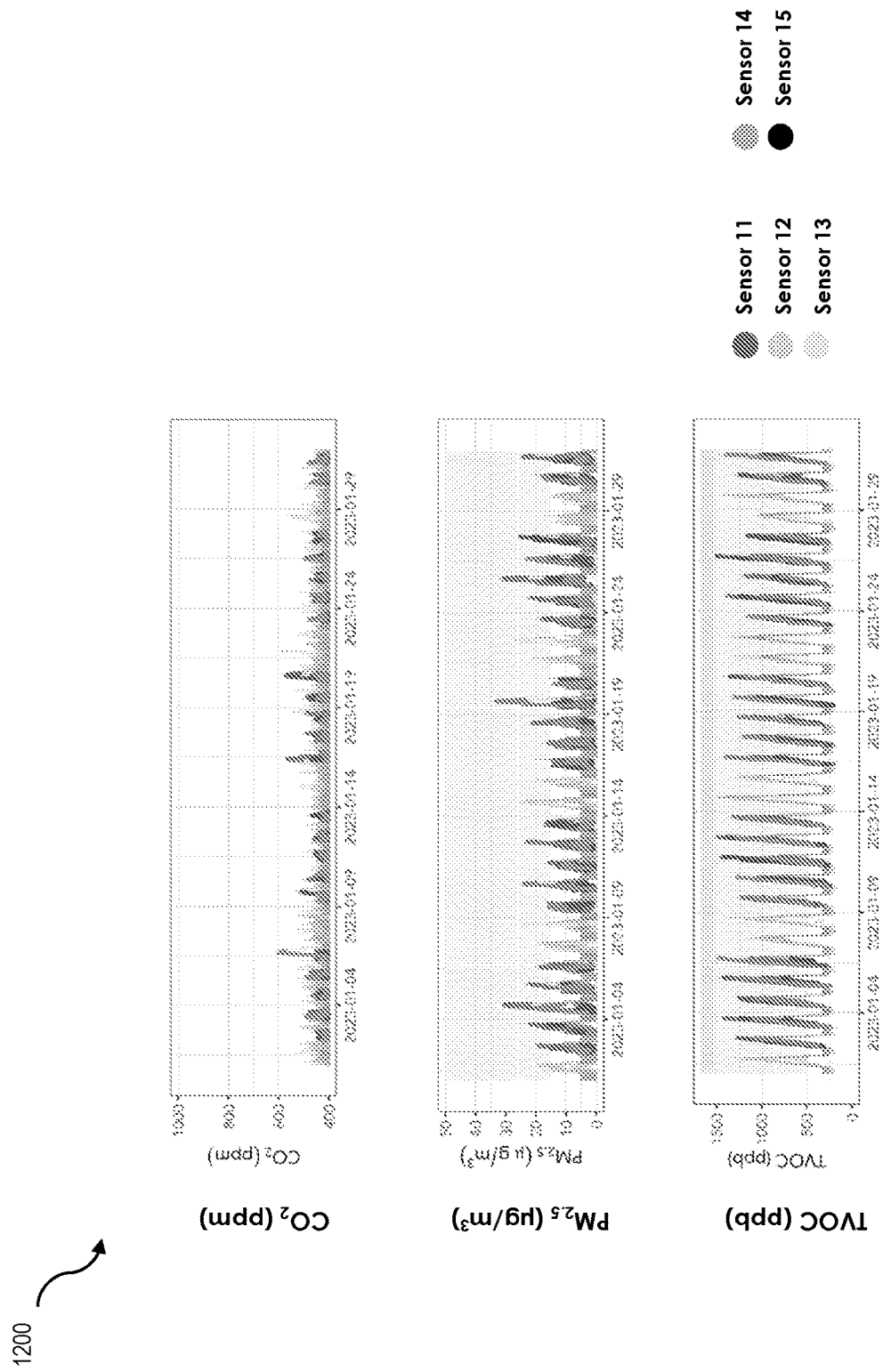
FIG. 12 illustrates an exemplary graphical user interface for displaying the distribution of data over time associated with sensors associated with a space (i.e., a floor) in a building.

FIG. 12 provides an example of a visualization for a timeseries 1200 in accordance with some embodiments of the present disclosure. As illustrated in FIG. 12, a report may be generated illustrating the timeseries visualization for each parameter for each floor. As shown, in some embodiments, timeseries data can be shown for each parameter separately in separate subplots within a graphical user interface. Each subplot may also illustrate each sensor separately. Accordingly, reports may be generated for each floor. For example, timeseries may be generated for temperature, RH, or noise from all sensors on a single floor over the reporting period. The timeseries plots can be used to identify sensors of interest.

Figure 13:
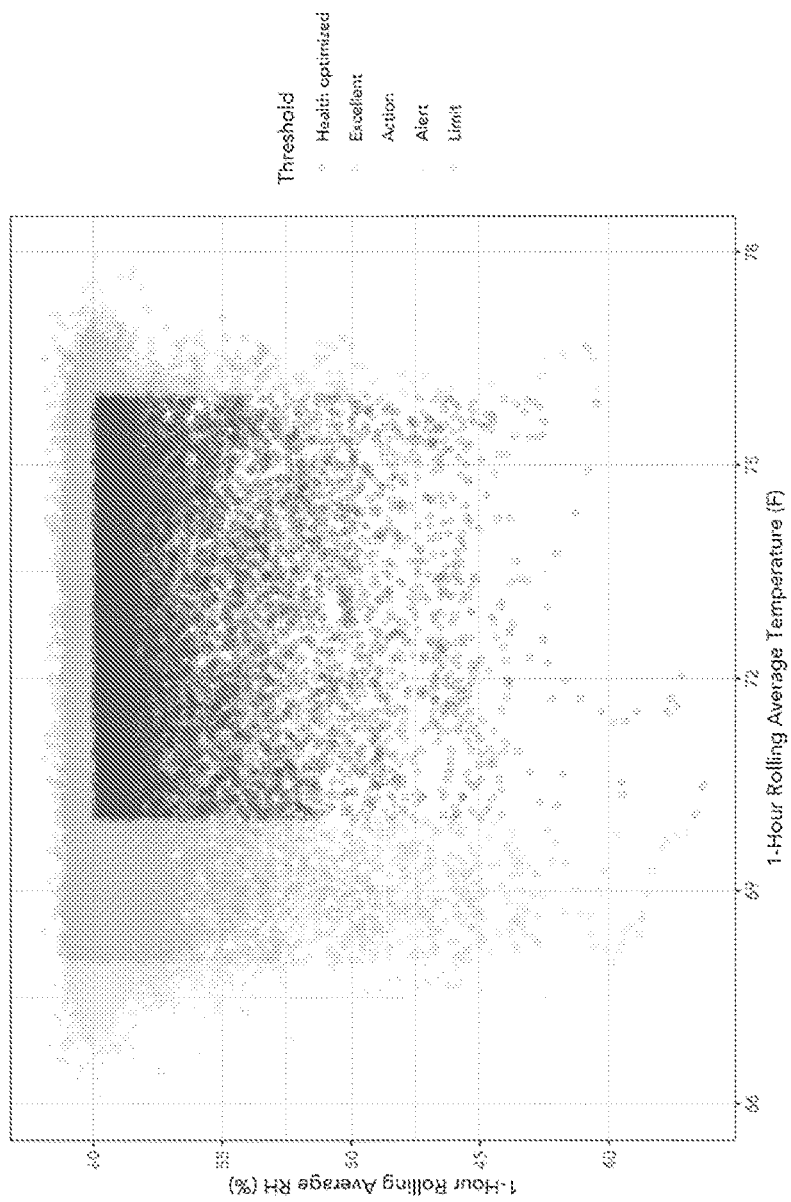
FIG. 13 illustrates an exemplary graphical user interface for displaying the distribution of data for two parameters obtained from sensors associated with a space in a building.

FIG. 13 provides an example of a visualization for temperature and relative humidity 1300. As illustrated in FIG. 13, a summary plot may be used to convey how measured temperature and RH may compare to exposure thresholds during the reporting period. As shown, a rolling average of temperature measurements may be plotted on the x-axis against a rolling average of relative humidity. The location of each data point may represent the rolling average temperature and relative humidity at a single point in the time during the occupied hours of the building. In some embodiments, points may be shaded or colored to represent the relationship between the data and the thresholds. In some embodiments, temperature and RH are scored together. For example, a temperature of 72 F and an RH of 40% would receive a score of Health Optimized, while a temperature of 72 F and an RH of 62% would receive a score of Excellent. Relative humidity, a measure of the amount of water vapor present in air expressed as a perentage of the amount needed for saturation at the same temperature. $RH_{out-x}$, where x=1, 6, or 11, is defined as x less than the RH that a parcel of outdoor air would have if its temperature was changed from current outdoor temperature to the current indoor temperature without changing the water content of the air. In some embodiments, when rolling averages fall in the Health Optimized and Excellent ranges, any negative impacts of thermal conditions on occupant health, productivity, and comfort are expected to be minimized. If rolling averages consistently fall in the Action range, which is not uncommon in some office buildings, the monitored area where the exceedances occurred may be evaluated for potential sources of suboptimal thermal conditions. When rolling averages consistently fall in the Alert and Limit ranges, the monitored area where the exceedances occurred should be evaluated and corrective actions should be identified. A graphical illustration for displaying the distribution of data for two parameters obtained from sensors in the building can be built for any suitable spatial scale including by floor, building, set of buildings and the like.

Figure 14:
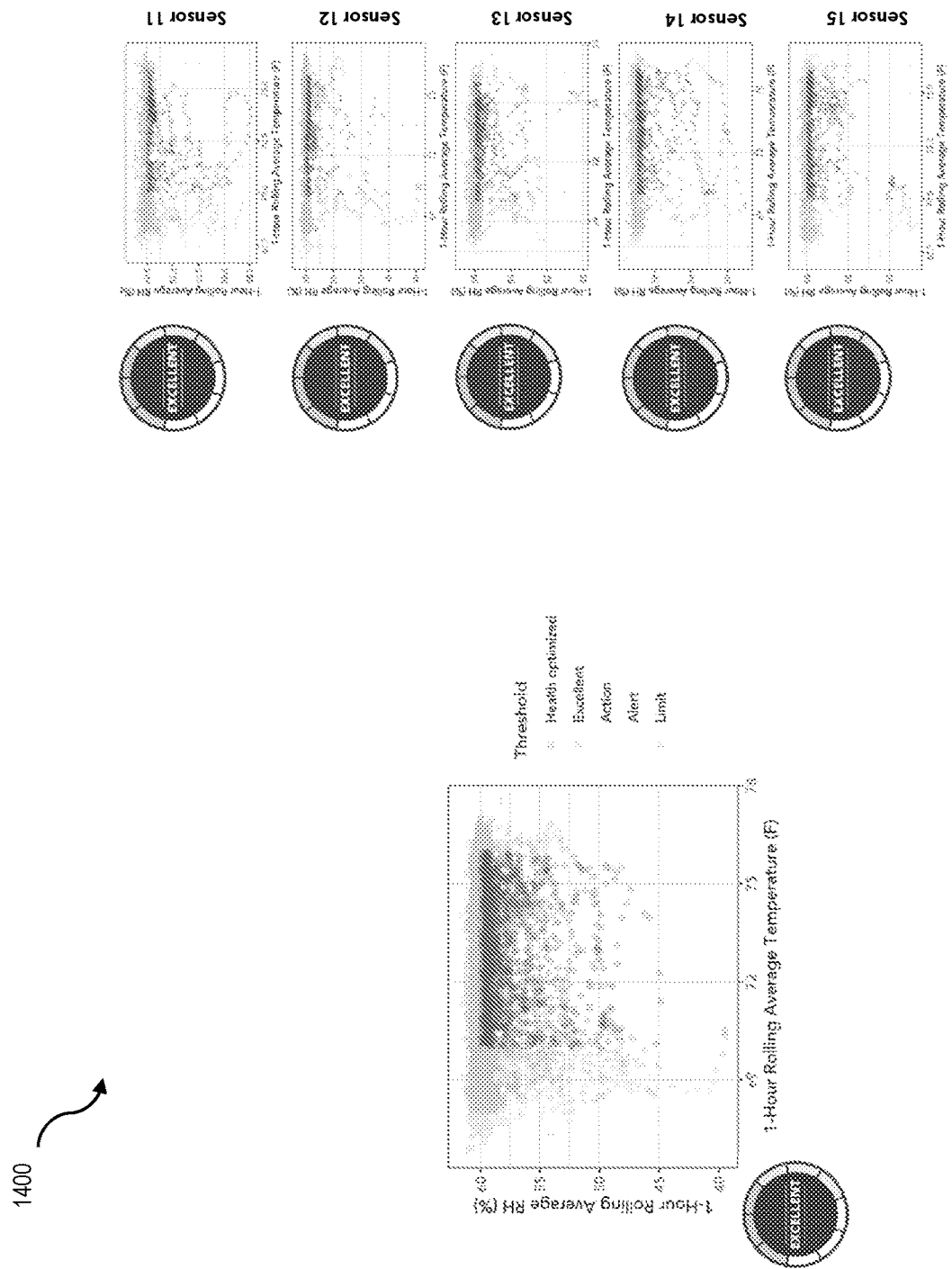
FIG. 14 illustrates an exemplary graphical user interface for displaying the distribution of data for two parameters obtained from sensors associated with a space (i.e., a floor) in a building.

FIG. 14 provides an example of a visualization for temperature and relative humidity 1400 across a plurality of floors in a commercial building. As shown, visualizations may be generated for each floor. In some embodiments, additional visualization elements such as badges that visually represent scores can be shown for each sensor and/or floor.

Figure 15:
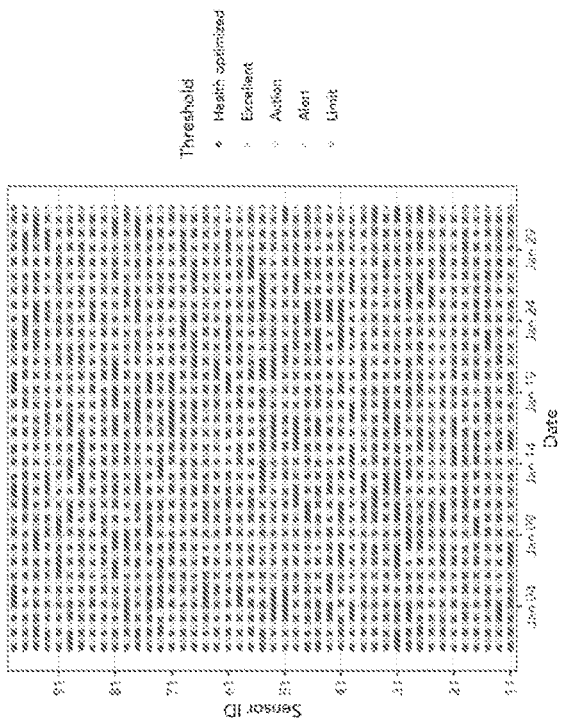
FIG. 15 illustrates an exemplary graphical user interface for displaying the distribution of a parameter over time associated with sensors associated with a space in a building.

FIG. 15 provides an example of a visualization for noise data in a noise map 1500. As illustrated in FIG. 15, a noise map 1500 may be used to convey how data points related to noise compared to thresholds over the reporting period. For example, the date may be plotted along the x-axis and the sensor ID may be plotted along the y-axis. The noise map 1500 may provide a summary for cleaned data from all the sensors for the entire reporting period, including the hours where the building is occupied or unoccupied. Each point may represent a rolling average of noise measurements, and the shape and/or color of each point may correspond to the threshold range where the average falls. The noise data map 1500 may provide a user with the ability to evaluate trends in data over space and time. Although a noise map is shown, similar visualizations for other parameters may be generated.

Figure 16:
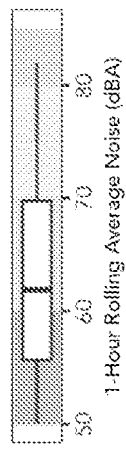
FIG. 16 illustrates an exemplary graphical user interface for displaying the distribution of a parameter over time associated with sensors associated with a space in a building.
Figure 16:
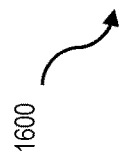

FIG. 16 provides an example of a visualization for a noise boxplot 1600. As shown, the noise boxplot 1600 may provide an indication of how noise measurements from a particular sensor compared to thresholds during the reporting period. The left side of the box may indicate the $25^{th}$ percentile of 1-hour rolling averages of noise measurements, the middle line in the box shows median of 1-hour rolling averages of noise measurements, and the right side of the box shows $75^{th}$ percentile of 1-hour rolling averages of noise measurements. The noise boxplot 1600 may also include bands to indicate the corresponding thresholds. The noise boxplot 1600 may include plotting rolling average of noise measurements (dBA) on the x-axis. Although noise measurements for a particular sensor are illustrated in FIG. 16, it is envisioned that similar noise boxplots can be developed for a whole portfolio of buildings, a single building's noise data, and/or a whole floor's noise data.

Figure 17:
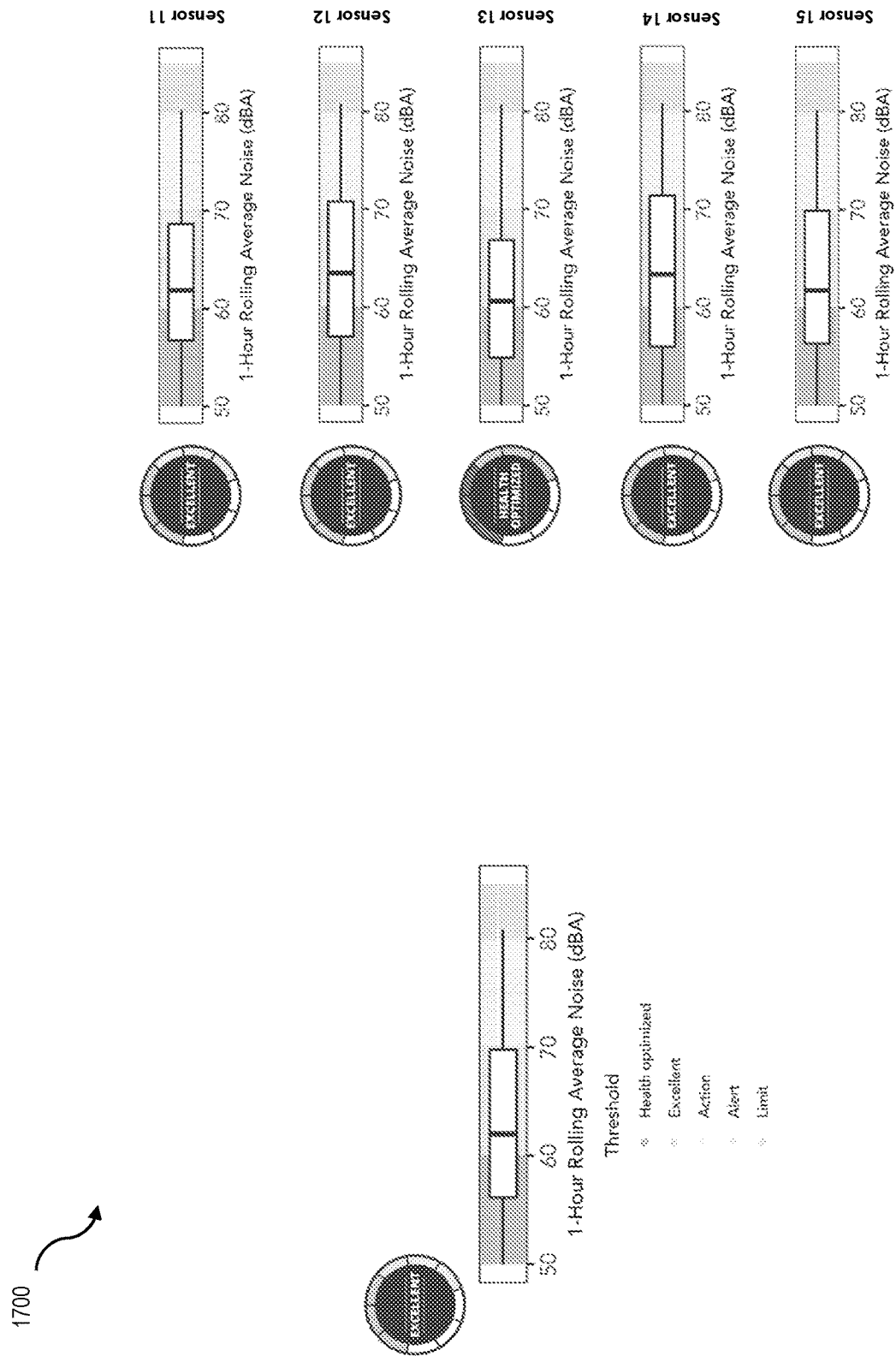
FIG. 17 illustrates an exemplary graphical user interface for displaying the distribution of a parameter over time associated with sensors associated with a space (i.e., a floor) in a building.

FIG. 17 provides an example of a visualization for the noise boxplot 1700. As shown, in some user interface a first portion of the graphical user interface may be configured to include a summary noise boxplot. A second portion of the graphical user interface can be configured to illustrate component parts of the data set contributing to the summary noise boxplot. For example, a noise boxplot for each floor and/or each sensor may be visualized separately in a second portion of the graphical user interface, as shown on the right panel of FIG. 17. In some embodiments, additional visualization elements such as badges that visually represent scores can be shown for each sensor and/or floor.

Figure 18:
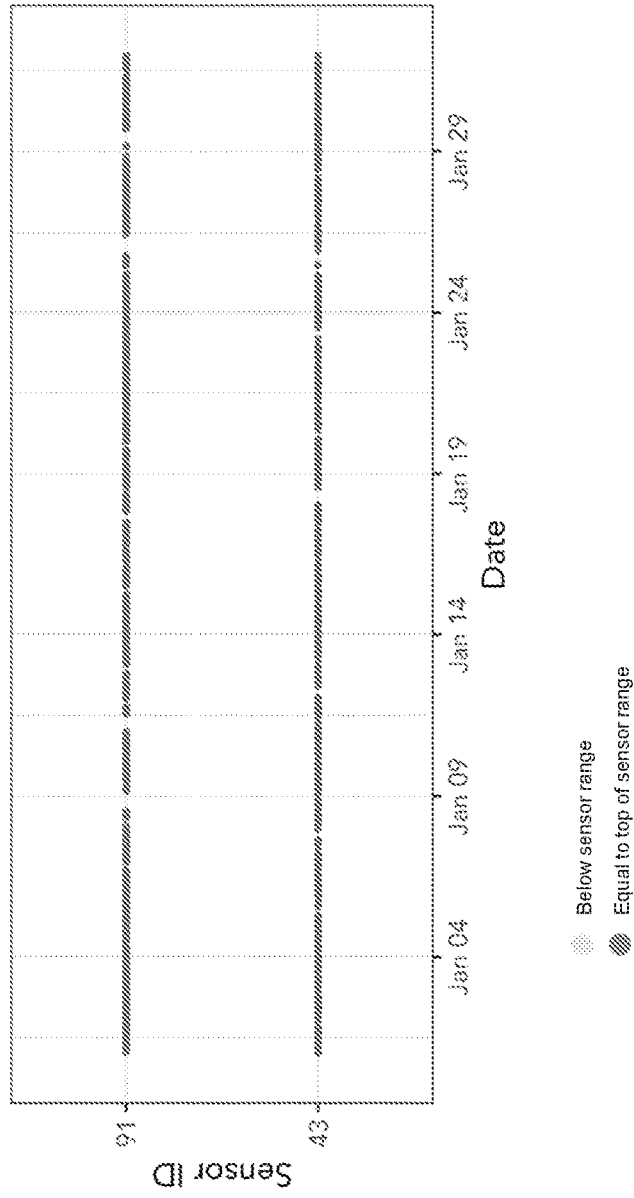
FIG. 18 illustrates an exemplary graphical user interface for displaying data quality.

FIG. 18 provides an example visualization for data quality checks. As shown, in some embodiments data quality checks may include timeseries plots of data that is outside of measurement ranges 1800. For example, data from sensors with more than 1% of data outside the sensor measurement ranges in the reporting period may be represented visually.

Figure 19:
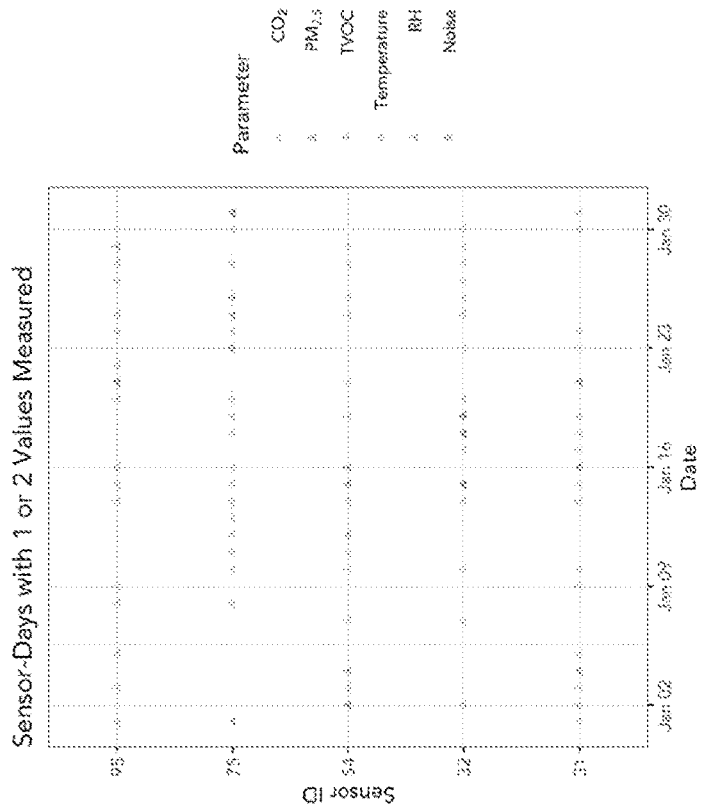
FIG. 19 also illustrates an exemplary graphical user interface for displaying data quality.

FIG. 19 provides a second example visualization for data quality checks. As shown, in some embodiments, data quality checks may include plots of sensors with abnormally low variation 1900. This plot 1900 flags sensors that may have issues with abnormally low variation, where individual parameters only took on one or two unique values.

Figure 20:
FIG. 20 illustrates an exemplary graphical user interface used for detecting sensor issues.

FIG. 20 illustrates an exemplary graphical user interface used for detecting sensor issues. For example, the IAQ map can be used to determine that a particular sensor (i.e., sensor 21) consistently senses data in the set category (i.e., Limit) for the duration of the entire time period.

Figure 21:
FIG. 21 illustrates an exemplary graphical user interface used for detecting a floor issue.
Figure 21:

FIG. 21 illustrates an exemplary graphical user interface used for detecting a floor issue. For example, the IAQ map can be used to determine that a particular floor underwent an event as shown by all of the sensors associated with a particular floor (e.g., Sensors 21-25, inclusive) sensing data belonging to the elevated categories (i.e., alert Limit) for the same time period.

Figure 22:
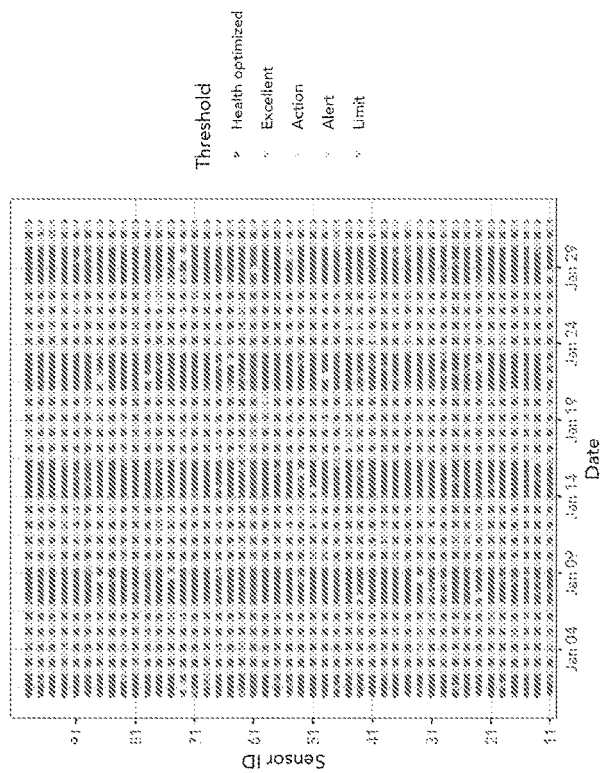
FIG. 22 illustrates an exemplary graphical user interface used for detecting a building issue.

FIG. 22 illustrates an exemplary graphical user interface used for detecting a building issue. For example, the IAQ map can be used to determine that a building underwent an event as shown by all of the sensors associated with a particular building sensing data belonging to elevated categories (i.e., alert) for the same time period (e.g., weekdays in January in the afternoons).

Other embodiments are within the scope and spirit of the disclosed subject matter. For example, the monitoring system described in this application can be used in facilities that have complex machines with multiple operational parameters that need to be altered to change the performance of the machines (e.g., building automation systems). Usage of the word "optimize"/"optimizing" in this application can imply "improve"/"improving."

Certain exemplary embodiments are described herein to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network. An algorithm can include a computer program. An algorithm can include computer executable instructions (e.g. that can be executed by a processor).

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a Read-Only Memory or a Random Access Memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor or phone, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web interface through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

What is claimed is:

1. A method comprising:
   receiving data characterizing a time-dependent first sensor data detected by a first sensor, a time-dependent second sensor data detected by a second sensor, a set of first threshold values associated with the first sensor, a set of second threshold values associated with the second sensor and a time window, wherein the first sensor and the second sensor are located in a first space of a building;
   calculating a first performance index based on the first sensor data and the time window and a second performance index based on the second sensor data and the time window;
   classifying the first performance index and the second performance index into one of a plurality of performance indicators characterizing respective human health risks of environmental conditions of the first space of the building on a health of building occupants, wherein the classification of the first performance index and the second performance index is based on comparison of the first performance index and the second performance index with the first set of threshold values and the second set of threshold values, respectively;
   determining a performance rating score for the first space by scoring the classification of first performance index and the second performance index within the plurality of performance indicators characterizing the respective human health risks of the environmental conditions of the first space of the building on the health of the building occupants, wherein the performance rating score characterizes a combined human health risk of the environmental conditions on the health of the building occupants;
   providing the performance rating score assigned to the first space in a first visualization in a graphical user interface; and
   updating the graphical user interface based on an input received from a user of the graphical user interface to display a second visualization comprising the performance rating score.

2. The method of claim 1, wherein calculating the first performance index includes:
   selecting a first portion of the time-dependent first sensor data that temporally spans from a first time to a second time, wherein the difference between the second time and the first time corresponds to the time window; and
   calculating the first performance index by averaging the first portion of the time-dependent first sensor data.

3. The method of claim 2, further comprising calculating a third performance index, the calculating includes:
   selecting a second portion of the time-dependent first sensor data that temporally spans from a third time to a fourth time, wherein the difference between the fourth time and the third time corresponds to the time window; and
   calculating the third performance index by averaging the second portion of the time-dependent first sensor data.

4. The method of claim 3, further comprising:
   classifying the first performance index to a first category of the plurality of categories; and
   classifying the third performance index to a second category of the plurality of categories, wherein the first performance index is greater than the first threshold value associated with the first sensor, and the second performance index is smaller than the first threshold value.

5. The method of claim 4, further comprising:
   rendering, in a graphical user interface, a first visual representation of the first category of the plurality of categories and a second visual representation of the second category of the plurality of categories;
   generating a first graphical object indicative of the first performance index;
   generating a second graphical object indicative of the third performance index; and
   rendering, in the graphical user interface, the first graphical object over the first visual representation and the second graphical object over the second visual representation.

6. The method of claim 5, wherein the first graphical object is rendered in a first region of the graphical user interface at a first time, wherein the first graphical object traverses from the first region of the graphical region to the first visual representation during a time period subsequent to the first time.

7. The method of claim 1, further comprising:
   rendering, in a graphical user interface, a visual representation of at least one of the first performance indicator, the second performance indicator, and the performance rating score of the first space for a first time period; and
   rendering in a graphical user interface a second visual representation of at least one of the first performance indicator, the second performance indicator, and the performance rating score of the first space for a second time period.

8. The method of claim 1, further comprising:
receiving environmental data including at least one of ventilation, infiltration, recirculation rates, heating filter type, airflow, space dimensions, and floor plans; and
determining a first sensor position for a first sensor and a second sensor position for a second sensor within the first space of the building.

9. The method of claim 1 further comprising:
receiving data characterizing a time-dependent third sensor data detected by a third sensor, and a set of third threshold values associated with the third sensor, wherein the third sensor is located in the first space of the building;
calculating a third performance index based on the third sensor data and the time window;
classifying the third performance index into one of a plurality of performance indicators wherein the classification of the third performance index is based on a comparison of the third performance index with the third set of threshold values; and
wherein determining the performance rating score for the first space further comprises scoring the classification of the third performance index within the plurality of performance indicators.

10. The method of claim 9, wherein the set of third threshold values associated with the third sensor corresponds to noise.

11. The method of claim 1, further comprising:
initiating at least one of a replacement in at least one of the first sensor or the second sensor, an adjustment in positioning of at least one of the first sensor or the second sensor, or a corrective action in a building automation system, or a building management system, responsive to user interaction with the performance rating score provided in the graphical user interface.

12. The method of claim 1, wherein the one of a plurality of performance indicators is indicative of the at least one of occupant comfort, health, or work performance.

13. The method of claim 1, further comprising:
generating a report comprising the performance rating score.

14. A system comprising:
at least one data processor;
memory coupled to the at least one data processor, the memory storing instructions to cause the at least one data processor to perform operations comprising:
receiving data characterizing a time-dependent first sensor data detected by a first sensor, a time-dependent second sensor data detected by a second sensor, a first set of threshold values associated with the first sensor, a second set of threshold values associated with the second sensor and a time window, wherein the first sensor and the second sensor are located in a first space of a building;
calculating a first performance index based on the first sensor data and the time window and a second performance index based on the second sensor data and the time window;
classifying the first performance index and the second performance index into one of a plurality of performance indicators characterizing respective human health risks of environmental conditions of the first space of the building on a health of building occupants, wherein the classification of the first performance index and the second performance index is based on comparison of the first performance index and the second performance index with the first set of threshold values and the second set of threshold values, respectively;
determining a performance rating score for the first space by scoring the classification of first performance index and the second performance index within the plurality of performance indicators characterizing the respective human health risks of the environmental conditions of the first space of the building on the health of the building occupants, wherein the performance rating score characterizes a combined human health risk of the environmental conditions on the health of the building occupants; and
providing the performance indicator assigned to the first space in a first visualization in a graphical user interface; and
updating the graphical user interface based on an input received from a user of the graphical user interface to display a second visualization comprising the performance rating score.

15. The system of claim 14, wherein calculating the first performance index includes:
selecting a first portion of the time-dependent first sensor data that temporally spans from a first time to a second time, wherein the difference between the second time and the first time corresponds to the time window; and
calculating the first performance index by averaging the first portion of the time-dependent first sensor data.

16. The system of claim 14, the operations further comprising:
rendering, in a graphical user interface, a visual representation of at least one of the first performance indicator, the second performance indicator, and the performance rating score of the first space for a first time period; and
rendering in a graphical user interface a second visual representation of at least one of the first performance indicator, the second performance indicator, and the performance rating score of the first space for a second time period.

17. The system of claim 14, the operations further comprising:
receiving environmental data including at least one of ventilation, infiltration, recirculation rates, heating filter type, airflow, space dimensions, and floor plans; and
determining a first sensor position for a first sensor and a second sensor position for a second sensor within the first space of the building.

18. The system of claim 14, wherein the one of a plurality of performance indicators is indicative of the at least one of occupant comfort, health, or work performance.

19. The system of claim 14, the operations further comprising:
generating a report comprising the performance rating score.

20. A computer program product comprising a non-transitory machine-readable medium storing instructions that, when executed by at least one programmable processor that comprises at least one physical core and a plurality of logical cores, cause the at least one programmable processor to perform operations comprising:
receiving data characterizing a time-dependent first sensor data detected by a first sensor, a time-dependent second sensor data detected by a second sensor, a first threshold value associated with the first sensor, a second threshold value associated with the second sensor and a time window, wherein the first sensor and the second sensor are located in a first space of a building;

calculating a first performance index based on the first sensor data and the time window and a second performance index based on the second sensor data and the time window;

classifying the first performance index and the second performance index into one of a plurality of performance indicators characterizing respective human health risks of environmental conditions of the first space of the building on a health of building occupants, wherein the classification of the first performance index and the second performance index is based on comparison of the first performance index and the second performance index with the first threshold value and the second threshold value, respectively;

determining a performance rating score for the first space by scoring the classification of first performance index and the second performance index within the plurality of performance indicators characterizing the respective human health risks of the environmental conditions of the first space of the building on the health of the building occupants, wherein the performance rating score characterizes a combined human health risk of the environmental conditions on the health of the building occupants;

providing the performance indicator assigned to the first space in a first visualization in a graphical user interface; and updating the graphical user interface based on an input received from a user of the graphical user interface to display a second visualization comprising the performance rating score.

* * * * *